US012779022B2

(12) United States Patent
Dastmalchi et al.

(10) Patent No.: US 12,779,022 B2
(45) Date of Patent: Nov. 3, 2026

(54) BIOCOMPATIBLE NANOCOMPOSITE HYDROGEL IMMUNOTHERAPY VACCINES AND METHODS OF USE THEREOF

(71) Applicant: University of Florida Research Foundation, Inc., Gainesville, FL (US)

(72) Inventors: Farhad Dastmalchi, Gainesville, FL (US); Maryam Rahman, Gainesville, FL (US); Thomas Ettor Angelini, Gainesville, FL (US); Hector R. Mendez-Gomez, Gainesville, FL (US); Elias Sayour, Gainesville, FL (US)

(73) Assignee: UNIVERSITY OF FLORIDA RESEARCH FOUNDATION, Gainesville, FL (US)

( * ) Notice: Subject to any disclaimer, the term of this patent is extended or adjusted under 35 U.S.C. 154(b) by 472 days.

(21) Appl. No.: 18/021,373

(22) PCT Filed: Aug. 13, 2021

(86) PCT No.: PCT/US2021/045958
§ 371 (c)(1),
(2) Date: Feb. 14, 2023

(87) PCT Pub. No.: WO2022/036231
PCT Pub. Date: Feb. 17, 2022

(65) Prior Publication Data

US 2024/0033333 A1 Feb. 1, 2024

Related U.S. Application Data

(60) Provisional application No. 63/065,901, filed on Aug. 14, 2020.

(51) Int. Cl.
*A61K 39/00* (2006.01)
*A61P 35/00* (2006.01)

(52) U.S. Cl.
CPC .......... *A61K 39/0011* (2013.01); *A61P 35/00* (2018.01); *A61K 2039/5154* (2013.01); *A61K 2039/5158* (2013.01); *A61K 2039/53* (2013.01); *A61K 2039/55522* (2013.01); *A61K 2039/6018* (2013.01); *A61K 2039/6093* (2013.01)

(58) Field of Classification Search
CPC ........ A61K 39/0011; A61K 2039/5154; A61K 2039/5158; A61K 2039/53; A61K 2039/55522; A61K 2039/6018; A61K 2039/6093; A61K 2039/80; A61K 2039/876; A61K 2039/55511; A61K 2039/55555; A61K 39/39; A61P 35/00
See application file for complete search history.

(56) References Cited

U.S. PATENT DOCUMENTS

| | | | |
|---|---|---|---|
| 10,441,528 B2 | 10/2019 | Alessi et al. | |
| 2007/0065467 A1 | 3/2007 | Krieg et al. | |
| 2017/0042995 A1 | 2/2017 | Ali et al. | |
| 2018/0243231 A1 | 8/2018 | Bencherif et al. | |
| 2022/0143210 A1* | 5/2022 | Olson | A61K 39/3955 |

FOREIGN PATENT DOCUMENTS

| | | | |
|---|---|---|---|
| JP | 05229934 A * | 9/1993 | |
| WO | 2010123971 A2 | 10/2010 | |
| WO | 2018044888 A1 | 3/2018 | |
| WO | 2019217593 A1 | 11/2019 | |
| WO | WO 2019/213308 A1 * | 11/2019 | |

OTHER PUBLICATIONS

Chen et al. Gene Therapy. 2018; 25: 556-567. (Year: 2018).*
Sayour et al. Int J Mol Sci. 2018; 19: 2890. (Year: 2018).*
Sayour et al. Oncoimmunology. 2017; 6(1): e1256527. (Year: 2017).*
Chen et al., "Scaffold-mediated Delivery for non-viral mRNA vaccines", Gene Therapy, 2018, vol. 25, pp. 556-567.
International Search Report mailed Nov. 30, 2021 in co-pending PCT Application No. PCT/US2021/045958.
Leitner, W. W., et al. (1999), "DNA and RNA-based vaccines: principles, progress and prospects," Vaccine, 18 (9-10), 765-777. doi:10.1016/s0264-410x(99)00271-6.
Liu, M. A. (2019), "A Comparison of Plasmid DNA and mRNA as Vaccine Technologies," Vaccines (Basel), 7(2). doi:10.3390/vaccines7020037.
McNamara, M. A., et al. (2015), "RNA-Based Vaccines in Cancer Immunotherapy," J Immunol Res, 2015, 794528. doi:10.1155/2015/794528.
Hubert P., et al., "Delivery of granulocyte-macrophage colony-stimulating factor in bioadhesive hydrogel stimulates migration of dendritic cells in models of human papillomavirus-associated (pre)neoplastic epithelial lesions," Antimicrob Agents Chemother. 2004;48(11):4342-4348. doi:10.1128/AAC.48.11.4342-4348.2004.
Song H., et al., "Injectable polypeptide hydrogel-based co-delivery of vaccine and immune checkpoint inhibitors improves tumor immunotherapy," Theranostics. 2019;9(8):2299-2314. Published Apr. 12, 2019. doi:10.7150/thno.30577.
Shao Y., et al., "Designable Immune Therapeutical Vaccine System Based on DNA Supramolecular Hydrogels," ACS Appl Mater Interfaces. Mar. 21, 2018;10(11):9310-9314. doi: 10.1021/acsami.8b00312. Epub Mar. 12, 2018; https://www.ncbi.nlm.nih.gov/pubmed/29484882.

(Continued)

*Primary Examiner* — David Browe
(74) *Attorney, Agent, or Firm* — Thomas | Horstemeyer, LLP

(57) ABSTRACT

The present disclosure includes biocompatible, nanocomposite hydrogel compositions and vaccines, where the compositions and vaccines include a biocompatible hydrogel material, a plurality of immune stimulating cytokines, such as CXCL9, and a plurality of nano liposomes loaded with mRNA molecules corresponding to a target antigen, such as for a condition to be treated. This disclosure also includes methods of making the biocompatible, nanocomposite hydrogel compositions and vaccines as well as methods of using the vaccines of the present disclosure to treat and/or prevent a disease in a subject.

16 Claims, 17 Drawing Sheets

(56) References Cited

OTHER PUBLICATIONS

Wang, et al., "Biomaterial-based scaffold for in situ chemo-immunotherapy to treat poorly immunogenic tumors," Nature Communications 11; 5696 (2020).
Shah, et al., "A biomaterial-based vaccine eliciting durable tumour-specific responses against acute myeloid leukaemia," Nature Biomedical Engineering 4, 40-51 (2020).

* cited by examiner

FIG. 11A
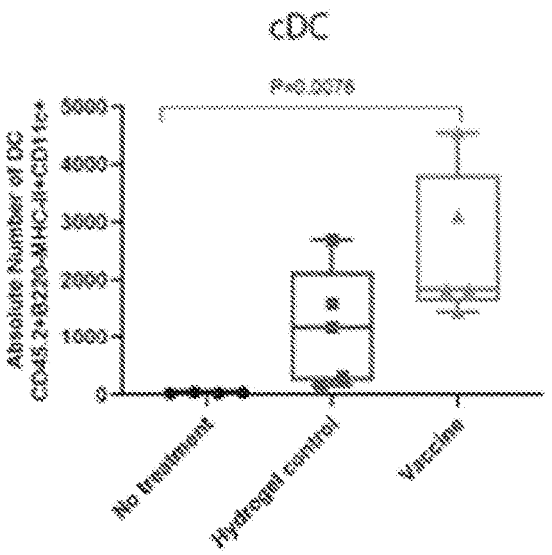
FIG. 11B
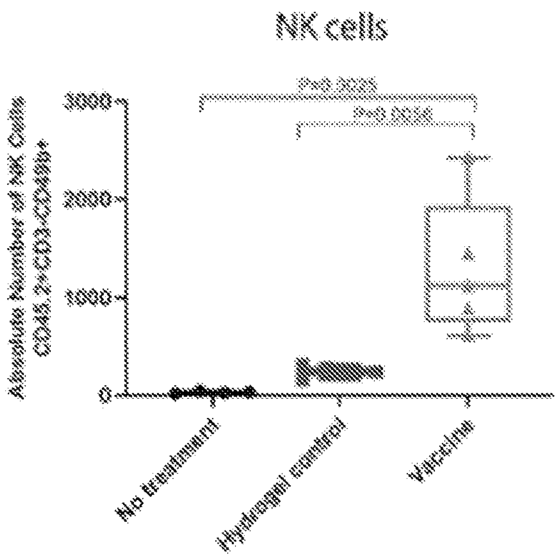
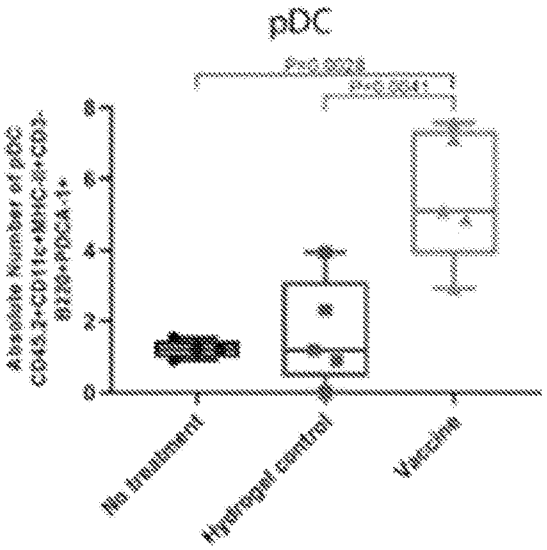
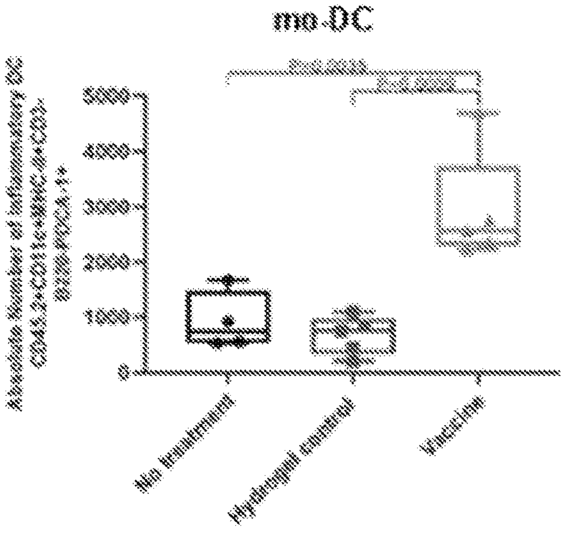
FIG. 11C
FIG. 11D

BIOCOMPATIBLE NANOCOMPOSITE HYDROGEL IMMUNOTHERAPY VACCINES AND METHODS OF USE THEREOF

CROSS REFERENCE TO RELATED APPLICATIONS

This application is the 35 U.S.C. § 371 national stage application of PCT Application No. PCT/US2021/0045958, filed Aug. 13, 2021, which application claims the benefit of U.S. Provisional Application No. 63/065,901, filed Aug. 14, 2020, both of which are hereby incorporated by reference herein in their entireties.

BACKGROUND

Much interest has been generated in the approach of activating the immune system against diseases such as cancer using immunotherapy and/or vaccines that utilize the host immune cells to attack cancer cells or other infectious diseases. Some such approaches are performed by delivering immune cells via infusion or vaccination. In some methodologies the immune cells are first harvested from the individual and engineered ex vivo to recognize a target (e.g., cancer cells, infectious disease cells, etc.). For example, in an approach known as DC vaccine immunotherapy, dendritic cells (DCs) with/without T cells can be "educated" ex vivo against certain tumor antigens. These primed DCs are then delivered back to patients to recognize and attack the tumor cells. These techniques are well-described, versatile against various types of cancer, and have led to FDA approved therapies.

However, many of these existing approaches have several limitations including, among others, an intensive and expensive production process, and significant production time. Such methodologies also require highly-skilled experts, which limits widespread use, availability, and accessibility. Other challenges to DC vaccine immunotherapy include limited survival of the educated DC cells once delivered to the patient and limited cell migration to the area of interest (lymph node or tumor), thereby resulting in a limited immune response in the patient.

SUMMARY

Briefly described, aspects of the present disclosure provide biocompatible, nano-composite hydrogel compositions and vaccines including the biocompatible, nanocomposite hydrogel compositions. Also provided are methods of making the biocompatible, nano-composite hydrogel compositions and vaccines as well as methods of using the vaccines of the present disclosure to treat and/or prevent a disease in a subject.

Biocompatible, nanocomposite hydrogel composition according to the present disclosure include a biocompatible hydrogel material; a plurality of CXCL9 molecules in the hydrogel; and a plurality of nano liposomes loaded with mRNA molecules corresponding to a target antigen for a specific disease. According to some aspects, the nano liposomes can be multi-layer vesicles. In some embodiments, the mRNA molecules correspond to a tumor antigen.

The present disclosure also provides vaccines including the biocompatible, nanocomposite, hydrogel compositions of the present disclosure.

Methods for making the biocompatible, nanocomposite hydrogel composition of the present disclosure include preparing mRNA loaded nano liposomes and then combining mRNA loaded nano liposomes with a CXCL9 composition and a biocompatible hydrogel composition. Preparing the mRNA loaded nano liposomes includes combining a mRNA composition that includes mRNA antigen in a carrier with a composition of nano liposomes. According to some embodiments, the mRNA composition and composition of nano liposomes are combined in a ratio of about 1:6 (mRNA:nano liposomes).

Other systems, methods, features, and advantages of the present disclosure will be or will become apparent to one with skill in the art upon examination of the following drawings and detailed description. It is intended that all such additional systems, methods, features, and advantages be included within this description, and be within the scope of the present disclosure.

BRIEF DESCRIPTION OF THE DRAWINGS

Further aspects of the present disclosure will be more readily appreciated upon review of the detailed description of its various embodiments, described below, when taken in conjunction with the accompanying drawings. The components in the drawings are not necessarily to scale, emphasis instead being placed upon clearly illustrating the principles of the present disclosure. Moreover, in the drawings, like reference numerals designate corresponding parts throughout the several views.

FIG. 8A is a graph illustrating chemotaxis potentiality of CXCL9, and FIGS. 8B-8D are images of immunofluorescence microscopy illustrating migration of NK cells in control (FIG. 8B), culture medium (FIG. 8C), and hydrogel (FIG. 8D).

FIG. 9A is a graph illustrating chemotaxis of human DCs, and FIGS. 9B-9D are images of immunofluorescence microscopy illustrating migration of h-mDCc in control (FIG. 9B), culture medium (FIG. 9C), and hydrogel (FIG. 9D).

FIG. 10A is a graph illustrating chemotaxis potentiality of CXCL9, and FIGS. 10B-10D are images of immunofluorescence microscopy illustrating migration of h-NK cells in control (FIG. 10B), culture medium (FIG. 10C), and hydrogel (FIG. 10D).

FIGS. 11A-11D are graphs illustrating in vivo analysis of immune cell recruitment to the site of hydrogel implantation. Type 2 classical DCs (cDC2) (FIG. 11A), and NK cells (FIG. 11B) were significantly increased 3 days after vaccination. Plasmacytoid dendritic cells (pDCs) (FIG. 11C) and inflammatory DCs (FIG. 11D) were increased at day 5 post vaccination. Mean and SD shown.

FIG. 13B is a digital image of IVIS imaging of tumor grown in vaccinated vs. control mice. FIGS. 13C and 13D illustrate measurement of survival (FIG. 13C) and tumor size (FIG. 13D) in B16F10-OVA tumor model of vaccinated mice vs. control group.

DETAILED DESCRIPTION

Figure 1:
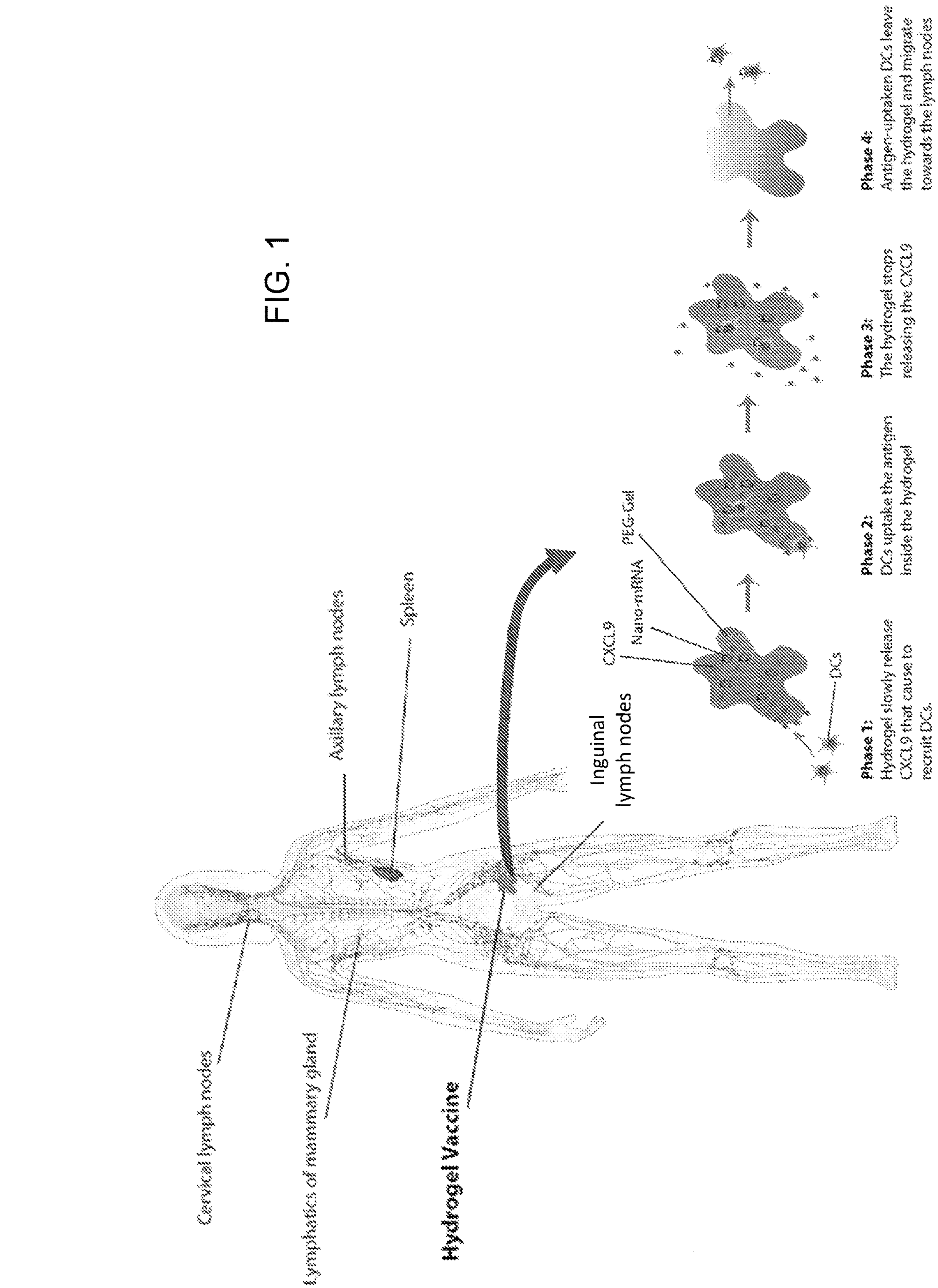
FIG. 1 is a schematic illustration of an embodiment of the biocompatible, nanocomposite hydrogel immunotherapy vaccine of the present disclosure demonstrating the mode of action in the body of a subject.

Before the present disclosure is described in greater detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit (unless the context clearly dictates otherwise), between the upper and lower limit of that range, and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of molecular biology, biochemistry, material science, medicine, and the like, which are within the skill of the art. Such techniques are explained fully in the literature.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20-25° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only and is not intended to be limiting. It is also possible in the present disclosure that steps can be executed in different sequence where this is logically possible.

All publications and patents cited in this specification are cited to disclose and describe the methods and/or materials in connection with which the publications are cited. Publications and patents that are incorporated by reference, where noted, are incorporated by reference as if each individual publication or patent were specifically and individually indicated to be incorporated by reference. Such incorporation by reference is expressly limited to the methods and/or materials described in the cited publications and patents and does not extend to any lexicographical definitions from the cited publications and patents. Any lexicographical definition in the publications and patents cited that is not also expressly repeated in the instant application should not be treated as such and should not be read as defining any terms appearing in the accompanying claims. Any terms not specifically defined within the instant application, including terms of art, are interpreted as would be understood by one of ordinary skill in the relevant art; thus, is not intended for any such terms to be defined by a lexicographical definition in any cited art, whether or not incorporated by reference herein, including but not limited to, published patents and patent applications. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

It must be noted that, as used in the specification and the appended claims, the singular forms "a," "an," and "the" include plural referents unless the context clearly dictates otherwise. Thus, for example, reference to "a cell" includes a plurality of cells. In this specification and in the claims that follow, reference will be made to a number of terms that shall be defined to have the following meanings unless a contrary intention is apparent.

As used herein, the following terms have the meanings ascribed to them unless specified otherwise. In this disclosure, "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein. "Consisting essentially of" or "consists essentially" or the like, when applied to methods and compositions encompassed by the present disclosure have the meaning ascribed in U.S. Patent law and the term is open-ended, allowing for the presence of more than that which is recited so long as basic or novel characteristics of that which is recited is not changed by the presence of more than that which is recited, but excludes prior art embodiments.

Prior to describing the various embodiments, the following definitions are provided and should be used unless otherwise indicated.

Definitions

In describing and claiming the disclosed subject matter, the following terminology will be used in accordance with the definitions set forth below.

As used herein, the term "biocompatible," with respect to a substance or fluid described herein, indicates that the substance or fluid does not adversely affect the short-term viability or long-term proliferation of a target biological particle within a particular time range.

The term "biodegradable" as used herein, generally refers to a material that will degrade or erode under physiologic conditions to smaller units or chemical species that are capable of being metabolized, eliminated, or excreted by the subject. The degradation time is a function of composition and morphology. Degradation times can be from hours to weeks.

As used herein, "organism", "host", and "subject" refers to any living entity comprised of at least one cell. A living organism can be as simple as, for example, a single isolated eukaryotic cell or cultured cell or cell line, or as complex as a mammal, including a human being, and animals (e.g., vertebrates, amphibians, fish, mammals, e.g., cats, dogs, horses, pigs, cows, sheep, rodents, rabbits, squirrels, bears, primates (e.g., chimpanzees, gorillas, and humans). As used herein, "patient" can refer to an organism, host, or subject in need of treatment.

The terms "treat", "treating", and "treatment" are an approach for obtaining beneficial or desired clinical results. Specifically, beneficial or desired clinical results include, but are not limited to, alleviation of symptoms, diminishment of extent of disease, stabilization (e.g., not worsening) of disease, delaying or slowing of disease progression, substantially preventing spread of disease, amelioration or palliation of the disease state, and remission (partial or total) whether detectable or undetectable. In addition, "treat", "treating", and "treatment" can also be therapeutic in terms of a partial or complete cure for a disease and/or adverse effect attributable to the disease. As used herein, the terms "prevent," "prophylactically treat," or "prophylactically treating" refers to completely, substantially, or partially preventing a disease/condition or one or more symptoms thereof in a host. Similarly, "delaying the onset of a condition" can also be included in "preventing/prophylactically treating" and refers to the act of increasing the time before the actual onset of a condition in a patient that is predisposed to the condition.

As used herein, "administering" refers to an administration that is oral, topical, intravenous, subcutaneous, transcutaneous, transdermal, intramuscular, intra-joint, parenteral, intra-arteriole, intradermal, intraventricular, intraosseous, intraocular, intracranial, intraperitoneal, intralesional, intranasal, intracardiac, intraarticular, intracavernous, intrathecal, intravireal, intracerebral, and intracerebroventricular, intratympanic, intracochlear, rectal, vaginal, by inhalation, by catheters, stents or via an implanted reservoir or other device that administers, either actively or passively (e.g. by diffusion) a composition the perivascular space and adventitia. For example, a medical device such as a stent can contain a composition or formulation disposed on its surface, which can then dissolve or be otherwise distributed to the surrounding tissue and cells. The term "parenteral" can include subcutaneous, intravenous, intramuscular, intra-articular, intra-synovial, intrasternal, intrathecal, intrahepatic, intralesional, and intracranial injections or infusion techniques.

As used herein, "agent" refers to any substance, compound, molecule, and the like, which can be biologically active or otherwise can induce a biological and/or physiological effect on a subject to which it is administered to. An agent can be a primary active agent, or in other words, the component(s) of a composition to which the whole or part of the effect of the composition is attributed. An agent can be a secondary agent, or in other words, the component(s) of a composition to which an additional part and/or other effect of the composition is attributed.

As used herein "cancer" can refer to one or more types of cancer including, but not limited to, acute lymphoblastic leukemia, acute myeloid leukemia, adrenocortical carcinoma, Kaposi Sarcoma, AIDS-related lymphoma, primary central nervous system (CNS) lymphoma, anal cancer, appendix cancer, astrocytomas, atypical teratoid/Rhabdoid tumors, basal cell carcinoma of the skin, bile duct cancer, bladder cancer, bone cancer (including but not limited to Ewing Sarcoma, osteosarcomas, and malignant fibrous histiocytoma), brain tumors, breast cancer, bronchial tumors, Burkitt lymphoma, carcinoid tumor, cardiac tumors, germ cell tumors, embryonal tumors, cervical cancer, cholangiocarcinoma, chordoma, chronic lymphocytic leukemia, chronic myelogenous leukemia, chronic myeloproliferative neoplasms, colorectal cancer, craniopharyngioma, cutaneous T-Cell lymphoma, ductal carcinoma in situ, endometrial cancer, ependymoma, esophageal cancer, esthesioneuroblastoma, extracranial germ cell tumor, extragonadal germ cell tumor, eye cancer (including, but not limited to, intraocular melanoma and retinoblastoma), fallopian tube cancer, gallbladder cancer, gastric cancer, gastrointestinal carcinoid tumor, gastrointestinal stromal tumors, central nervous system germ cell tumors, extracranial germ cell tumors, extragonadal germ cell tumors, ovarian germ cell tumors, testicular cancer, gestational trophoblastic disease, hary cell leukemia, head and neck cancers, hepatocellular (liver) cancer, Langerhans cell histiocytosis, Hodgkin lymphoma, hypopharyngeal cancer, islet cell tumors, pancreatic neuroendocrine tumors, kidney (renal cell) cancer, laryngeal cancer, leukemia, lip cancer, oral cancer, lung cancer (non-small cell and small cell), lymphoma, melanoma, Merkel cell carcinoma, mesothelioma, metastatic squamous cell neck cancer, midline tract carcinoma with and without NUT gene changes, multiple endocrine neoplasia syndromes, multiple myeloma, plasma cell neoplasms, mycosis fungoides, myelodyspastic syndromes, myelodysplastic/myeloproliferative neoplasms, chronic myelogenous leukemia, nasal cancer, sinus cancer, non-Hodgkin lymphoma, pancreatic cancer, paraganglioma, paranasal sinus cancer, parathyroid cancer, penile cancer, pharyngeal cancer, pheochromocytoma, pituitary cancer, peritoneal cancer, prostate cancer, rectal cancer, Rhabdomyosarcoma, salivary gland cancer, uterine sarcoma, Sezary syndrome, skin cancer, small intestine cancer, large intestine cancer (colon cancer), soft tissue sarcoma, T-cell lymphoma, throat cancer, oropharyngeal cancer, nasopharyngeal cancer, hypoharyngeal cancer, thymoma, thymic carcinoma, thyroid cancer, transitional cell cancer of the renal pelvis and ureter, urethral cancer, uterine cancer, vaginal cancer, cervical cancer, vascular tumors and cancer, vulvar cancer, and Wilms Tumor.

As used herein "infectious diseases" can refer to one or more types of infections including, but not limited to viral infections including, but not limited to, human immunodeficiency virus (HIV), hepatitis A, B and C, human papillomavirus (HPV), influenza, respiratory syncytial virus infection, adenovirus infection, parainfluenza virus infection, corona virus infection, measles, mumps, and rubella, polio, rabies, etc.; bacterial infections including, but not limited to, cholera, diphtheria, dysentery, bubonic plague, tuberculosis, typhoid, typhus, bacterial meningitis, otitis media, pneumonia, tuberculosis, gastritis, sinusitis, urinary tract infections (UTIs), skin infections, sexually transmitted infections (STIs), etc..

As used herein with reference to the relationship between DNA, cDNA, cRNA, RNA, mRNA, protein/peptides, and the like "corresponding to" or "encoding" (used interchangeably herein) refers to the underlying biological relationship between these different molecules. As such, one of skill in the art would understand that operatively "corresponding to" can direct them to determine the possible underlying and/or resulting sequences of other molecules given the sequence of any other molecule which has a similar biological relationship with these molecules. For example, from a DNA sequence an RNA sequence can be determined and from an RNA sequence a cDNA sequence can be determined.

As used herein, "culturing" can refer to maintaining cells under conditions in which they can proliferate and avoid senescence as a group of cells. "Culturing" can also include conditions in which the cells also or alternatively differentiate.

As used herein, "isolated" means separated from constituents, cellular and otherwise, in which the polynucleotide, peptide, polypeptide, protein, antibody, lipid, molecule, particle, or fragments thereof, are normally associated with in nature. A non-naturally occurring polynucleotide, peptide, polypeptide, protein, antibody, or fragments thereof, do not require "isolation" to distinguish it from its naturally occurring counterpart.

The term "nanoparticle" as used herein includes a nanoscale deposit of a homogenous or heterogeneous material. (Nanoparticles may be regular or irregular in shape and may be formed from a plurality of co-deposited particles that form a composite nanoscale particle. Nanoparticles may be generally spherical in shape or have a composite shape formed from a plurality of co-deposited generally spherical particles. Exemplary shapes for the nanoparticles include, but are not limited to, spherical, rod, elliptical, cylindrical, disc, and the like. In some embodiments, the nanoparticles have a substantially spherical shape. Similarly, a "nano liposome" refers herein to a nanoscale vesicle or particle made of lipids. Exemplary nano liposomes may have a hollow core that can contain other materials.

As used herein, "pharmaceutically acceptable carrier or excipient" refers to a carrier or excipient that is useful in preparing a pharmaceutical formulation that is generally safe, non-toxic, and is neither biologically or otherwise undesirable, and includes a carrier or excipient that is acceptable for veterinary use as well as human pharmaceutical use. A "pharmaceutically acceptable carrier or excipient" as used in the specification and claims includes both one and more than one such carrier or excipient.

As used herein, "therapeutic" can refer to treating, healing, and/or ameliorating a disease, disorder, condition, or side effect, or to decreasing in the rate of advancement of a disease, disorder, condition, or side effect. A "therapeutically effective amount" can therefore refer to an amount of a compound that can yield a therapeutic effect.

As used herein the terms "CXCL9 protein," "CXCL9 molecule," "CXCL9 chemokine," and "CXCL9" all refer to the same compound.

Some of the following abbreviations are used herein: Gelvac-Vaccine: biocompatible nanocomposite hydrogel vaccine; DCs: Dendritic cells; NKs: Natural Killer cells; PEG-Gel: polyethylene glycol gel.

Discussion

In accordance with the purpose(s) of the present disclosure, as embodied and broadly described herein, embodiments of the present disclosure, in some aspects, relate to compositions, systems, and methods for in vivo vaccine immunotherapy for treatment and/or prevention of cancer, infectious diseases, and other conditions. Embodiments of such devices, kits and methods facilitate and/or provide compositions and methods to modulate a hosts' immune cells in situ to recognize and attack disease causing cells/entities.

As described above, current approaches to vaccine immunotherapy for treatment of cancer and other diseases include dendritic cell (DC) vaccine immunotherapy. In such approaches, a patient's dendritic cells (DCs) are harvested and treated ex vivo (e.g., by exposure to cancer cells, antigens from tumor cells, etc.) such that the cells become primed to recognize a desired target antigen. The "educated" DCs are then re-introduced into the patient. Although some such approaches have been FDA approved and have had some success, the DC vaccine is not consistently effective and has limitations involving the difficulty, time, and expense of preparing the cells ex vivo, the survival of the prepared DCs after re-introduction to the patient, and limited migration to lymph nodes/tumor or other target sites. In contrast, the biocompatible, nanocomposite hydrogel immunotherapy vaccines (also sometimes referred to herein as "Gelvac") of the present disclosure overcome many of the limitations of DC vaccine immunotherapy. The hydrogel immunotherapy vaccines of the present disclosure recruit, modulate, and disseminate the subject's immune cells, particularly antigen presenting cells (APC's) (e.g., DCs, killer cells (KCs) and T cells) in vivo. The hydrogel immunotherapy vaccines also enhance antigen uptake, antigen presentation, and migration of DCs or other APCs in situ leading to more efficient immune vaccines. The hydrogel compositions and the methods of the present disclosure focus on an in vivo acting hydrogel vaccine that releases a chemokine signal for recruitment of host APCs to the hydrogel. Once in the hydrogel, the APCs uptake mRNA antigen to activate the APCs to the target antigen. The modified/activated APCs subsequently leave the hydrogel to exert systemic effects to combat a specific condition (e.g., cancer, infectious disease, etc.). An embodiment of the hydrogel, the vaccine elements, and this process is illustrated in FIG. 1.

Previous groups have evaluated the use of hydrogels for drug delivery, but focus on the degradability of the hydrogel for releasing drug or other active agent rather than features of the hydrogel such as porosity and density, which are related to the migration of immune cells into, within, and out of the hydrogel. In embodiments, the hydrogel of the present disclosure is a micro-porous hydrogel designed for slow-release, cellular infiltration, and maintaining cell viability. Some studies have also attempted to use hydrogels with various components to induce immune response in vivo but with limited success. Such approaches were unable to introduce a target antigen inside the hydrogel effectively or non-aggressively.

Other approaches have also evaluated different chemokines for recruiting immune cells to a specific location and/or for activating/enhancing immune response, but it is not believed any other approaches have used CXCL9 or recognized the ability of CXCL9 to recruit a wider variety of immune cells than other chemokines, as demonstrated in the example below. As shown, CXCL9 unexpectedly outperformed other chemokines in the ability to recruit multiple types of DC's including, but not limited to, bone marrow derived DC (BMDC), circulating DC (cDC), lymphatic tissue resistance DC (pDC), and DC2.4, as well as natural killer (NK) cells and T cells (e.g., CD8 T cells). Additionally, while previous groups have used DNA as an immunogenic antigen to present to for modulation of DCs, the compositions and methods of the present disclosure utilize mRNA. While mRNA is more immunogenic than DNA cell lysate, or total cell components, (McNamara, Nair, & Holl, 2015; Leitner, Ying, & Restifo, 1999; Liu, 2019) it is temperature sensitive and susceptible to degradation in vivo, thus making it a poor choice for in vivo applications. However, in the compositions of the present disclosure, the mRNA is effectively protected from degradation inside the hydrogel by encapsulation in multi-layer nano-liposomes.

Thus, embodiments of the present disclosure include a composition/system of a biocompatible, nanocomposite, hydrogel vaccine that includes the following primary components: a biocompatible hydrogel material, CXCL9 as an immune stimulating compound, and an mRNA target antigen, where the mRNA is encapsulated in lipid nanoparticles. The above components will be described in greater detail in the following description and the examples below.

According to aspects of the disclosure, the hydrogel of the compositions/vaccines of the present disclosure include a biocompatible hydrogel material. In embodiments the hydrogel material is a water-based polyethylene glycol (PEG) gel. In embodiments, the biocompatible hydrogel has a micro-porous structure to allow for release of CXCL9 and any other signaling molecules and migration by host APCs (e.g., DCs, T cells, KCs, etc.) into, within, and out of the hydrogel. The hydrogel also carries and protects the mRNA antigen.

In embodiments of the vaccines of the present disclosure, the hydrogel is formed from polyacrylamide microgels that have anionic groups (e.g., methacrylic acid), and others that have zwitterionic groups (e.g., carboxybetaine methacrylate, aka CBMA). Any anionic microgels are suitable to generate the hydrogel of the present disclosure due to their safety for living cells. In embodiments, the hydrogels of the present disclosure are PEG-based hydrogels. In embodiements the PEG has a molecular weight of about 250 Da to 10,000 Da, such as for instance, about 700 Da. Other candidate microgels include, but are not limited to, hyaluronic acid, alginate, dextran, or combinations of hydrogels. In some embodiments, the hydrogel can also be made from and/or include PEG-based hydrogels that have cationic groups (e.g., dimethylaminoethyl methacrylate, aka DMAEMA). Other candidate cationic groups include, but are not limited to, L-Lysine or D-Lysine.

The hydrogels of the present disclosure are microgels. As used herein "microgels" refers to micron-scale hydrogel spheres/particles that are packed together to form a solid-like substance with micron-sized pores between the packed spheres. It was previously found that cationic microgels that formed from quaternized ammonia group (e.g., quaternized 2-(dimethylamino)-ethyl methacrylate, aka qDMAEMA) were not safe for cells and could exhibit toxicity to cells; thus, anionic/zwitterionic microgel materials may be preferred. However, the PEG-based hydrogels with cationic groups as mentioned above were found suitable and non-toxic. In embodiments, the average size of the microgel particles is from about 1 micron to 100 microns. In embodiments, each micron-sized hydrogel sphere has a characteristic polymer mesh size of anywhere from about 1 nm and 100 nm. The micro-porous nature of the material comes from the open interstitial space between the packed spheres of the hydrogel. Different polymers or combinations of polymers can be used to reach the desired pore sizes to allow immune cells to easily penetrate and move within the hydrogel. In embodiments the pores have an average size of about 30 nanometers to 10 micrometers. Also, the hydrogels of the present disclosure have a viscosity suitable for injection by needles. In some embodiments the viscosity is from about 0.1 pa s and 10 Pa s (where Pa s indicates "Pascal-seconds").

In embodiments of making the hydrogels of the present disclosure, the hydrogel is formed from an organic and aqueous phase. In an embodiment, to prepare the organic phase, an organic solvent (such as, but not limited to kerosene) is combined with an emulsifier, such as but not limited to Polyglycerol polyricinoleate (PGPR), (5-10 mg/ml of kerosene). The aqueous phase can be prepared by combining a polymer selected from PEG (e.g., PEG, PEGa, PEGda, or other polyacrylamide microgels or combinations thereof) in an aqueous salt solution (e.g., water and 10% salt solution, such as APS). The organic and aqueous phases can be combined with agitation (e.g., homogenization at a speed of about 7000 rpm) for about 5 to 15 minutes. The mixture can then be purged with a gas, such as nitrogen, for a time of about 30 to about 60 minutes in order to create pores. The resulting composition can then be polymerized. For instance, the composition can be combined with a free radical stabilizer (such as Tetramethylethylenediamine (TEMED), etc). and stirred or agitated (e.g., for about 30 to 60 minutes) to polymerize the composition, forming the preliminary hydrogel. Other solvents, such as, but not limited to, oil/fat solvents or suitable extractants (such as ether, or other suitable solvents or extractants) can then be added to the preliminary formed hydrogel composition and dried (e.g., by desiccation with vacuum, etc.) to form the final hydrogel.

In aspects of the present disclosure, the hydrogel compositions/vaccines of the present disclosure include a plurality of CXCL9 molecules in the hydrogel. In embodiments, the CXCL9 molecules are present in an amount of about 250 ng/ml to 1500 ng/ml, such as, but not limited to about 500 ng/ml.

The hydrogel compositions/vaccines of the present disclosure also include mRNA molecules corresponding to a target antigen for a specific disease/condition. For instance, the mRNA can be a specific antigen for cancer, tumor, or infectious disease. In embodiments, the antigen may be a tumor antigen derived from a tumor in the subject to be treated. In embodiments, the antigen may be derived from a known infectious disease (e.g., bacteria, virus, etc.). The target antigen should be an antigen specific to the tumor, disease, or condition to be treated in order to activate the subject's immune cells to recognize and attack the specific disease cells/particles. mRNA has strong immunogenic potentiality and can induce the immune system against the specific antigen. For instance, in embodiments the mRNA in the hydrogel compositions/vaccines of the present disclosure can be total tumor mRNA or specific targeted mRNA, with no specific limitation on the type, size, or amount of mRNA included, as such can be determined based on the condition to be treated, severity of condition, tolerance of the patient, etc. The hydrogel compositions/vaccines of the present disclosure can include various amounts of mRNA. For instance, in embodiments, a vaccine hydrogel composition of the present disclosure can include 1 to 50 μg of mRNA, such as for example about 10 μg, but there is no specific limitation. The vaccines can include the mRNA component in different kinds/sizes or amounts as appropriate and determined based on the condition to be treated, the characteristics of the patient, and the like.

According to aspects of the present disclosure, the mRNA antigens of the hydrogel compositions are at least partially encapsulated in a nano liposome (also sometimes referred to herein as lipid nanoparticles). The nano liposomes can be made of a single layer or multi-layer of lipids. For instance, in embodiments, nano liposomes of the present disclosure can be made of single or multi-layer phospholipids, such as, but not limited to single layer or multi layers of Dioleoyl-3-trimethylammonium propane (DOTAP). Other phospholipids can be used, such as, but not limited to dioleoylphosphatidylethanolamine (DOPE), dioleoylphosphatidylcholine (DOPC), and dioleoylphosphatidylglycerol (DOPG). In embodiments, the nano liposomes are lipid vesicles having an average diameter of about 70 nm to about 200 nm. The compositions of the present disclosure can have a heterogenous population of liposomes ranging in size. The nano liposomes loaded with the mRNA can be formed by an emulsion process, such as a water/PBS emulsion process described in greater detail in the examples below. The immune cells, such as DC's, that migrate into the hydrogel composition can phagocyte the nano liposomes to acquire the mRNA inside the nano liposomes.

Due to the flexibility of this technology, the hydrogel can be formulated to hold any needed concentration/volume of mRNA/liposomes, with dosage amounts that can be determined based on factors such as condition to be treated, severity of condition, health, age, gender, and size of patient, etc. For purposes of illustration, in an embodiment, an amount of at least about 1 μg mRNA, can be loaded into about 5-10 μg of nano liposomes. In embodiments, each dosage of vaccine (e.g., per injection) can include about 1 to 50 μg of mRNA. In embodiments, the formed mRNA antigen containing nano liposomes are included in the hydrogel composition in an amount of about 5 μg/total volume of composition to about 550 μg/total volume of composition (such as about 6-10 μg/total volume of composition).

In an illustrative embodiment, a hydrogel composition/vaccine of the present disclosure can include about 50-60% hydrogel, 30-40% nano liposome (made of a material, such as, but not limited to, one or more typical phospholipids used to package nucleic acids, such as DOTAP, DOPE, DOPC, and DOPG, etc.), 10-20% PBS per total volume, including 5-10 ppm of mRNA and 0.25-1.5 ppm of CXCL9 per total volume.

The following is just an illustrative example for preparing the above combination: 10 μg of mRNA is prepared and added to PBS, then a solution of nanoliposome material is added on top of it (in this step, it is not agitated, but kept at room temperature for about 15 to 20 minutes up to an hour or more, during which time the nano liposomes will encapsulate the mRNA). Next, 500 ng/total volume of CXCL9 is added to the combination of mRNA-loaded nano liposomes, and the hydrogel is added to the whole combination. The final combination is then mixed gently, such as by pipetting or other mixing methodologies.

The present disclosure also includes methods of making the biocompatible, nanocomposite hydrogel compositions described herein. In embodiments, the nano liposomes containing mRNA antigen are made by combining a composition including the mRNA antigen with a nano liposome composition. In an embodiment, a composition of nano liposomes is made of DOTAP as described above and in greater detail in the examples below. Then the DOTAP nano liposome composition is combined on top of mRNA prepared in PBS and allowed to combine for an amount of time, e.g., about 5-30 min, such as 15 min. For example, a composition mRNA/PBS (1 μg/ul) can be combined with a nano liposome (DOTAP) composition at a ratio of about 1 to 6 at room temperature.

After formation of the mRNA-loaded nano liposomes, CXCL9 (e.g., 500 ng/ml of total volume) is added to the formed nano liposomes. Then, the CXCL9/nano liposome composition is combined with hydrogel. In embodiments the mRNA-nano liposome-CXCL9 composition is combined with hydrogel in a ratio of about 1:1 (V/V). For example, some embodiments of hydrogel compositions/vaccines of the present disclosure are made according to the methods of the present disclosure with a combination of about 53.3% hydrogel, about 40% mRNA-loaded nanoliposome and about 6.6% PBS, where the liposome/PBS combination contains about 10 μg/volume of mRNA and 500 ng/ml of CXCL9.

Aspects of the present disclosure also include methods of treating (as defined above, treating can include preventing) a condition (e.g., cancer, or other disease) by administering the biocompatible, nanocomposite, hydrogel vaccine of the present disclosure to a subject in need of treatment for (or at risk of developing) the condition. In embodiments, the disease is cancer and the mRNA is a mRNA corresponding to an antigen for a tumor cell associated with the cancer. In embodiments, the mRNA antigen is from a tumor cell obtained from the subject to be treated. Thus, the antigen can be obtained from/associated with the patient's own tumor cells. In embodiments, the disease is cancer, such as, but not limited to breast cancer, prostate cancer, lymphatic cancer, brain cancer, lung cancer, bone cancer, pancreatic cancer, and the like. In an embodiment the disease to be treated is an infectious disease (e.g., caused by an infectious agent such as, but not limited to, bacteria, virus, and fungi), and the mRNA antigen is obtained from the infectious agent associated with the disease to be treated. Generally, the mRNA antigen should be specific to the target disease to be treated in order to activate the patient's immune cells to the infectious agent, cancer cells, etc. for the condition to be treated.

In embodiments the biocompatible, nanocomposite, hydrogel vaccine of the present disclosure can be administered to a subject subcutaneously, via injection into the mammary fat pad, injection in a tumor site, via intracranial implantation, as well as other methods of delivery known to those of skill in the art.

Additional details regarding the methods, systems, and compositions, of the present disclosure are provided in the Examples below. The specific examples below are to be construed as merely illustrative, and not limitative of the remainder of the disclosure in any way whatsoever. Without further elaboration, it is believed that one skilled in the art can, based on the description herein, utilize the present disclosure to its fullest extent.

It should be emphasized that the embodiments of the present disclosure, particularly, any "preferred" embodiments, are merely possible examples of the implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure and protected by the following claims.

The following examples are put forth so as to provide those of ordinary skill in the art with a complete disclosure and description of how to perform the methods and use the compositions and compounds disclosed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figures of the numerical value. In addition, the phrase "about 'x' to 'y'" includes "about 'x' to about 'y'".

ASPECTS

The following listing of exemplary aspects supports and is supported by the disclosure provided herein.

Aspect 1. A biocompatible, nanocomposite hydrogel composition comprising: a biocompatible hydrogel material; a plurality of CXCL9 molecules in the hydrogel; and a plurality of nano liposomes loaded with mRNA molecules corresponding to a target antigen for a specific disease.

Aspect 2. The biocompatible, nanocomposite hydrogel composition of aspect 1, wherein the hydrogel material is a micro-porous hydrogel material.

Aspect 3. The biocompatible, nanocomposite hydrogel composition of any of aspects 1-2, wherein the hydrogel material is a water-based polyethylene glycol (PEG) hydrogel.

Aspect 4. The biocompatible, nanocomposite hydrogel composition of any of aspects 1-3, wherein the CXCL9 molecules are present in a concentration of about 250 to 1500 ng/ml of the hydrogel material.

Aspect 5. The biocompatible, nanocomposite hydrogel composition of any of aspects 1-4, wherein the mRNA molecules correspond to a tumor antigen.

Aspect 6. The biocompatible, nanocomposite hydrogel composition of any of aspects 1-4, wherein the mRNA molecules correspond to an infectious disease antigen.

Aspect 7. The biocompatible, nanocomposite hydrogel composition of any of aspects 1-6, wherein the nano liposomes comprise lipid vesicles having an average diameter of about 70 nm to 200 nm.

Aspect 8. The biocompatible, nanocomposite hydrogel composition of any of aspects 1-7, wherein the nano liposomes comprise multi-layer vesicles of dioleyl-3-trimethylammonium propane (DOTAP).

Aspect 9. The biocompatible, nanocomposite hydrogel composition of any of aspects 1-8, wherein the nano liposomes include about 1 μg mRNA to about 5-10 μg of nano liposomes.

Aspect 10. The biocompatible, nanocomposite hydrogel composition of any of aspects 1-10 wherein the composition comprises about 5 μg-550 μg mRNA loaded liposomes per total volume of composition.

Aspect 11. A vaccine comprising the biocompatible nanocomposite hydrogel of any of aspects 1-10.

Aspect 12. A vaccine of aspect 11 comprising about 10 μg of mRNA per vaccine.

Aspect 13. A method of treating or preventing a disease in a subject, the method comprising: administering a biocompatible nanocomposite hydrogel vaccine, wherein the vaccine comprises the biocompatible nanocomposite hydrogel of any of aspects 1-10.

Aspect 14. The method of aspect 13, wherein the disease is cancer and wherein the mRNA antigen is from a tumor cell associated with the cancer.

Aspect 15. The method of aspect 14, wherein the mRNA antigen is derived from a tumor cell in the subject to be treated.

Aspect 16. The method of aspect 13, wherein the disease is an infectious disease caused by an infectious agent selected from the group consisting of: bacterium, virus, and fungus, and wherein the mRNA antigen is from the infectious agent associated with the disease to be treated.

Aspect 17. A method of making a biocompatible, nanocomposite hydrogel composition, the method comprising:

preparing mRNA loaded nano liposomes by combining a mRNA composition comprising mRNA antigen in a carrier with a composition of nano liposomes;

combining mRNA loaded nano liposomes with a CXCL9 composition and a biocompatible hydrogel composition.

Aspect 18. The method of aspect 17, wherein the mRNA composition and composition of nano liposomes are combined in a ratio of about 1:6 (mRNA:nano liposomes).

Aspect 19. The method of any of aspects 17-18, wherein the mRNA composition comprises mRNA in phosphate buffered saline (PBS) and wherein the composition of nano liposomes comprises multi-layer vesicles of dioleyl-3-trimethylammonium propane (DOTAP).

Aspect 20. The method of any of aspects 17-19, wherein the mRNA composition and composition of nano liposomes are combined at room temperature for about 15 or more.

Aspect 21. The method of any of aspects 17-20, wherein the CXCL9 composition is added to mRNA loaded nano liposomes to form a mRNA-nano liposome-CXCL9 composition prior to combining with the hydrogel composition, and wherein the mRNA-nano-liposome-CXCL9 composition and the hydrogel composition are combined in a ratio of about 1:1 (v/v).

Aspect 22. The method of any of aspects 17-20, wherein the biocompatible, nanocomposite hydrogel composition includes about 50 to 60% by volume hydrogel, about 30 to 40% by volume nano liposomes, about 10 to 20% by volume PBS, about 5 to 10 ppm of mRNA per total volume and about 0.25 to 1.5 ppm of CXCL9 per total volume.

EXAMPLES

Now having described the embodiments of the disclosure, in general, the examples describe some additional embodiments. While embodiments of the present disclosure are described in connection with the example and the corresponding text and figures, there is no intent to limit embodiments of the disclosure to these descriptions. On the contrary, the intent is to cover all alternatives, modifications, and equivalents included within the spirit and scope of embodiments of the present disclosure.

Example 1—Preparation and Characterization of Hydrogel Vaccine "Gelvac"

The present example describes immunotherapy approaches to modulate a subject's immune cells in situ by designing and using a biocompatible nanocomposite hydrogel vaccine (also referred to herein as "Gelvac"). This composition/system allows the recruitment of DCs and T cells in vivo within the patient once the hydrogel is implanted. Therefore, there is no need for generating and preparing the DCs or T cells ex vivo as in previous approaches. Moreover, the lifespan of the cells will not be limited as it is with cells that are given after ex vivo manipulation.

As illustrated in FIG. 1, by implanting the Gelvac-Vaccine subcutaneously/intracranially or injecting into the mammary fat pad, CXCL9 chemokine will be slowly released and will recruit DCs and T cells within the hydrogel. DCs will uptake the loaded-targeted antigen (nano-mRNA). Subsequently, DCs will present the mRNA antigen to T cells. Finally, T cells will be stimulated against the loaded-specific antigen and will kill the antigen through migration to tumor site or by circulating in the whole body. This innovative treatment strategy can generate an immune response in vivo in a host against diverse pathogens including cancer cells or microbes.

Materials and Methods

Hydrogel Preparation

The hydrogel used in the present example was formed from an organic and aqueous phase. To prepare the organic phase, an organic solvent, kerosene was combined with an emulsifier, polyglycerol polyricinoleate (PGPR) at 5-10 mg/ml of kerosene. The aqueous phase was prepared by combining a PEG polymer or combination (e.g., PEG, PEGa, PEGda, or other polyacrylamide microgels or combinations thereof, see table below for various combinations used in the present example) in an aqueous salt solution (e.g., water and 10% salt solution, such as APS). The organic and aqueous phases were combined with agitation (e.g., homogenization at a speed of about 7000 rpm) for about 5 to 15 minutes. The mixture was then purged with nitrogen for a time of about 30 to about 60 minutes in order to create pores. The resulting composition was then combined with the free radical stabilizer Tetramethylethylenediamine (TEMED) and stirred or agitated for about 30 to 60 minutes) to polymerize the composition, forming the preliminary hydrogel. Then oil/fat solvents or suitable extractants (such as ether, etc) were added to the preliminary formed hydrogel composition and dried (e.g., by desiccation with vacuum, etc.) to form the final hydrogel.

Specific combinations and procedures for exemplary PEG microgels for the present example are described in the table and steps below.

TABLE 1

Polymer concentrations for PEG micro-gels (Hydrogel)

| Polymer Concentration (wt %) | PEGa 50% stock | PEGda 25% stock | APS 10% stock | Water |
|---|---|---|---|---|
| 25 wt % | 73.91 | 2.18 | 2.25 | 71.66 |
| 20 wt % | 59.13 | 1.74 | 2.25 | 86.88 |
| 15 wt % | 44.35 | 1.31 | 2.25 | 102.10 |

1. Preparing Organic Phase: for providing 1 liter of the base, 3.g gram of Polyglycerol polyricinoleate (PGPR) is mixed with 500 mL of Kerosene and the composition is stirred for 15 minutes.
2. Preparing Aqueous Phase: 2.25 g of Ammonium persulfate (APS) (10% solution), 73.91 g of PEGa, 2.18 g of PEDda and 71.66 g of water are combined and swirled for 2 minutes.
3. The organic and aqueous phases are combined and homogenized for 5 minutes at 7000 rpm.
4. The above solution is purged with Nitrogen for 1 hour.
5. Then above composition is combined with 3 ml of Tetramethylethylenediamine (TEMED)Temed and stirred for 1 hour.
6. After adding ether to above composition, it is desiccated overnight in vacuum oven to reach the final hydrogel.

Hydrogel Migration Assay

Figure 2B:
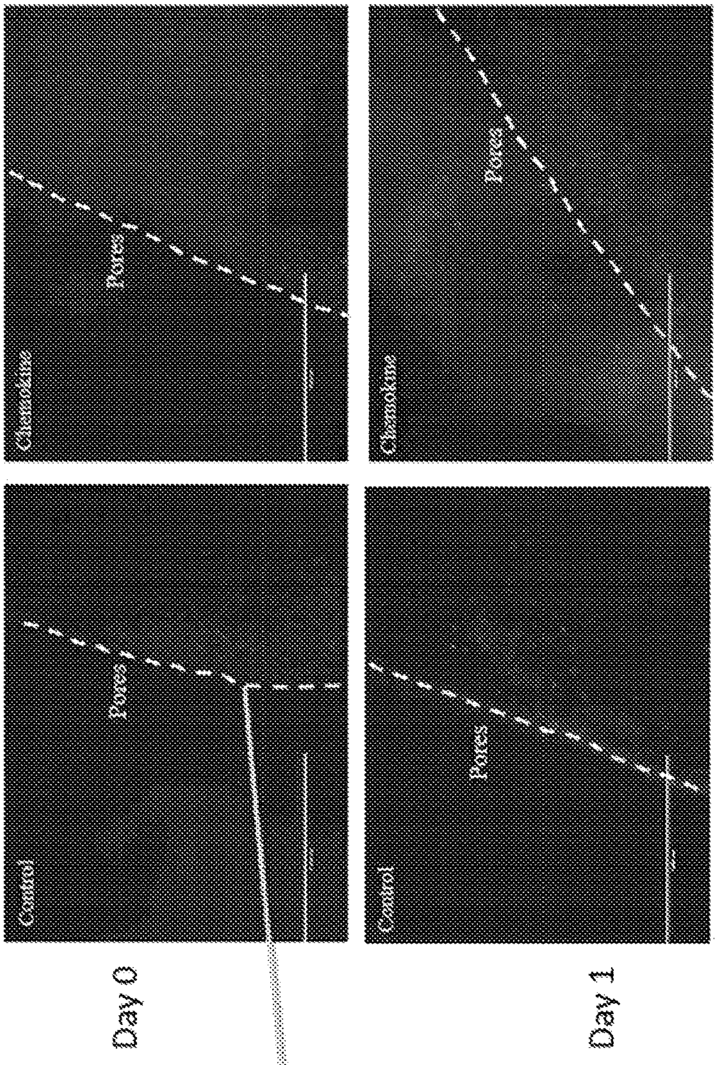
FIG. 2B is a series of images of immunofluorescence microscopy visualization of DC migration into the hydrogel and survival.
Figure 2A:
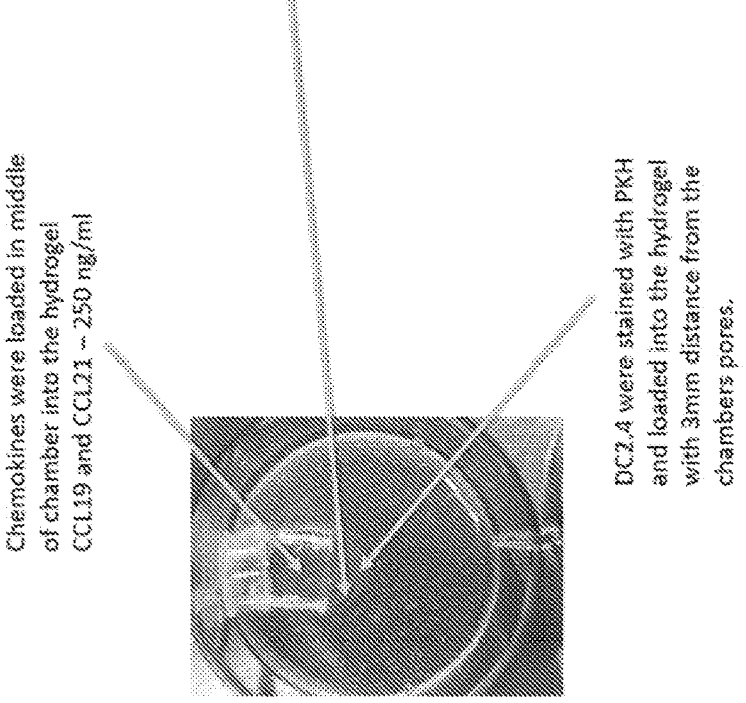
FIG. 2A is a digital image of a hydrogel of the present disclosure.

A container with an isolated inner chamber having pores was provided. The 25 wt % hydrogel (as described in table 1, above) was loaded into the container, with the hydrogel containing the CXCL9 and CCL21 chemokines (500 ng/ml) located inside the inner chamber and hydrogel without chemokines outside of the chamber. DCs were loaded into the hydrogel in the portion of the container front of the pores (e.g., outside the chamber), as illustrated in FIG. 2A. DCs were observed for migration into the chamber that contains chemokine by passing through pores 24 hours after culturing.

In Vitro Trans-Well Migration Assay of Mouse DCs

CXCL3, CXCL9, CCL19, and CCL21 (500 ng/ml) separately were added inside the hydrogel, and the culture medium in the lower chamber of the trans-well plate to evaluate the chemotaxis potentiality. The Control group had the same culture medium without chemokines. DCs were isolated from mouse bone-marrow, spleen and peripheral blood by using the mouse DC magnetic isolation kit and were loaded into upper chamber. DCs that migrated into the lower chamber were counted after 8 hours.

In Vitro Trans-Well Migration Assay of Mouse NK Cells

CXCL9 (500 ng/ml) was added inside the hydrogel and the culture medium in the lower chamber of the trans-well plate to evaluate the chemotaxis potentiality. The Control group had the culture medium without CXCL9. Mouse NK cells were isolated from spleen by magnetic mouse NK cell isolation kit. NK cells were stained with Pan NK1.1 (CD49b) antibody (PE color) and loaded in the upper chamber of the trans-well plate. Migration was observed with immunofluorescence microscopy and migrated NK cells into the lower chamber were counted after 8 hours.

Chemokine Release Assay

To determine and quantify the release of CXCL9 from the hydrogel, hydrogel was loaded with 500 ng/ml CXCL9. The hydrogel was located in the bottom of the wells in a 24 well-plate, and PBS was added on top of the hydrogel. PBS was collected at different time points to evaluate the amount of released CXCL9, and fresh PBS was replaced each time. Released CXCL9 was quantified with ELISA.

In Vitro Trans-Well Migration Analysis of T Cells

Naïve T cells were not activated, and activated T cells were activated in vitro with conA for four days before trans-well migration assay. CXCL9 was loaded inside the hydrogel and added in the culture medium in the lower chamber of trans-well plate to evaluate the chemotaxis potentiality. The control group had the culture medium without CXCL9. T cells were loaded in upper chamber of trans-well plate. Migrated T cells into the lower chamber were counted after 8 hours.

Antigen Uptake Assay

Antigen uptake by murine BM-DCs in hydrogel, culture medium was measured and compared. Antigen tested was FITC-OVA; control group had no antigen. Antigen uptake was measured, and DCs could uptake the antigen inside the hydrogel. Cells were incubated with FITC-OVA, antigen uptake was evaluated as mean fluorescence intensity (MFI) of FITC signal, and frequency of OVA+ DCs. DCs were stained with PKH21.

Antigen Presenting Assay

Antigen presenting assay was performed for DCs that migrated into the hydrogel by using GFP-mRNA-Nanoparticles, and GFP expression was visualized by immunofluorescence microscopy. DCs were stained with PKH21.

In Vitro Trans-Well Migration Analysis of Monocyte-Derived Dendritic Cells

In vitro trans-well migration analysis of human monocyte-derived dendritic cells (h-mDCc) was performed as follows. CXCL9 (500 ng/ml) was added inside the hydrogel and the culture medium in the lower chamber of the trans-well plate to evaluate the chemotaxis potentiality. The Control group had the culture medium without CXCL9. H-mDCs were isolated from PBMC by using the human DC magnetic isolation kit and were loaded into upper chamber. H-mDCs were stained with Nuc-Blue™ staining kit (Blue color), and migration of the h-mDCs was observed via immunofluorescence microscopy.

In Vitro Trans-Well Migration Analysis of Human Natural Killer (h-NK)

In vitro trans-well migration analysis of human Natural Killer (h-NK) cells was performed as follows. CXCL9 (500 ng/ml) was added inside the hydrogel and the culture medium in the lower chamber of the trans-well plate to evaluate the chemotaxis potentiality. The Control group had the culture medium without CXCL9. Human NK cells isolated from PBMC by using the NK magnetic isolation kit and were loaded into upper chamber. NK cells were stained with Nuc-Blue™ staining kit (Blue color), and location of the migrated h-NK cells was observed via immunofluorescence microscopy.

Results and Discussion

A hydrogel was generated from Polyethylene Glycol (PEG) as described above. The hydrogel was placed in an isolated chamber as shown in FIG. 2A within a culture dish, and the chamber had pores. Chemokines CCL19 and CCL21 (250 ng/ml) were also loaded into the hydrogel inside the chamber within the container. Dendritic cells (DC2.4) were loaded into additional hydrogel located in the container but outside of the chamber about 3 mm distance from the chamber pores. For control, another culture dish was set up in the same manner but without chemokines in the hydrogel within the chamber. As shown in FIG. 2B, DC's did not migrate in the control group, but in the chemokine group, the DCs migrated into the chamber that contains chemokine by passing through pores. Images were taken 24 hours after culturing. DCs were stained with PKH21. This demonstrated that the hydrogel was nontoxic, and that DCs could survive and migrate inside the hydrogel.

Figure 3A:
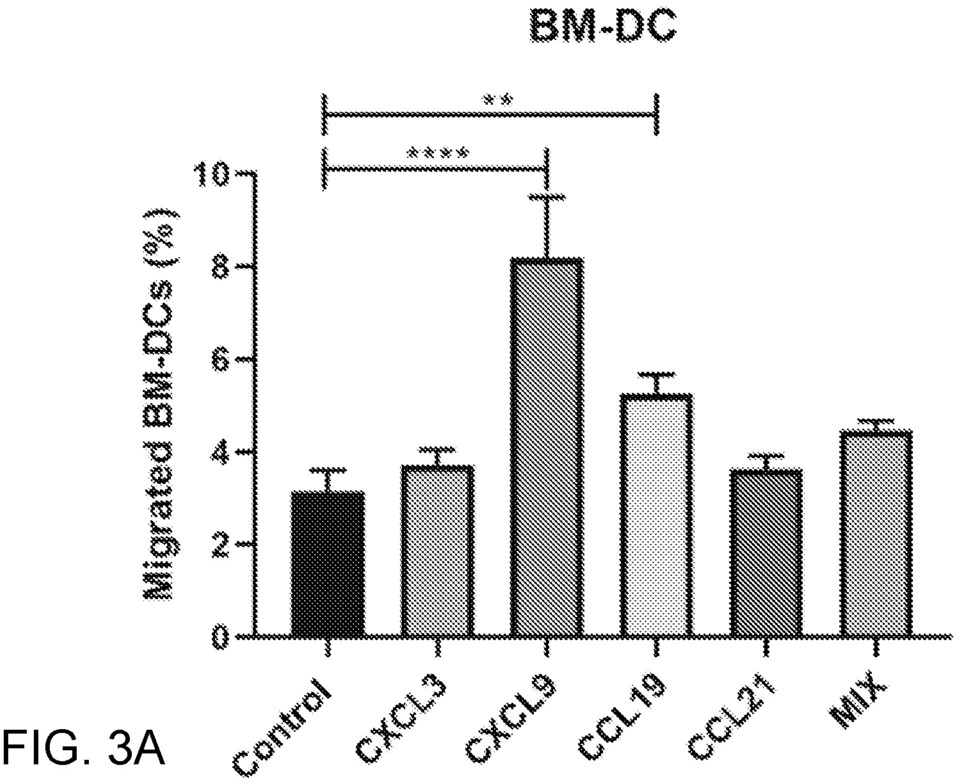
FIGS. 3A-3C are a series of graphs illustrating in vitro trans-well migration analysis of bone marrow-derived DCs (BM-DC) (FIG. 3A), spleen DCs (FIG. 3B), and circulating peripheral blood DCs (FIG. 3C) in the presence of different chemokines.
Figure 3B:
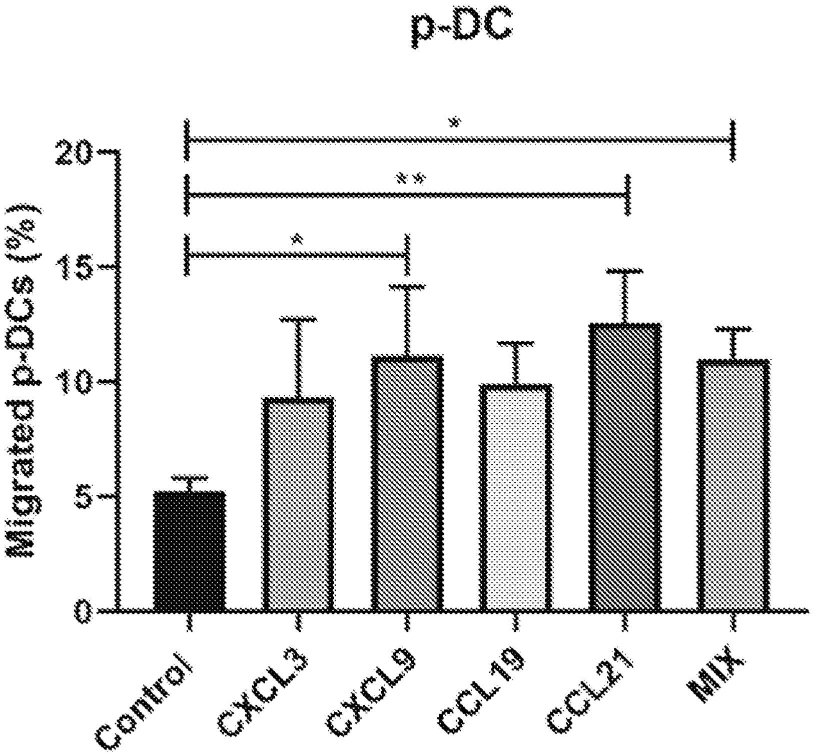
Figure 3C:
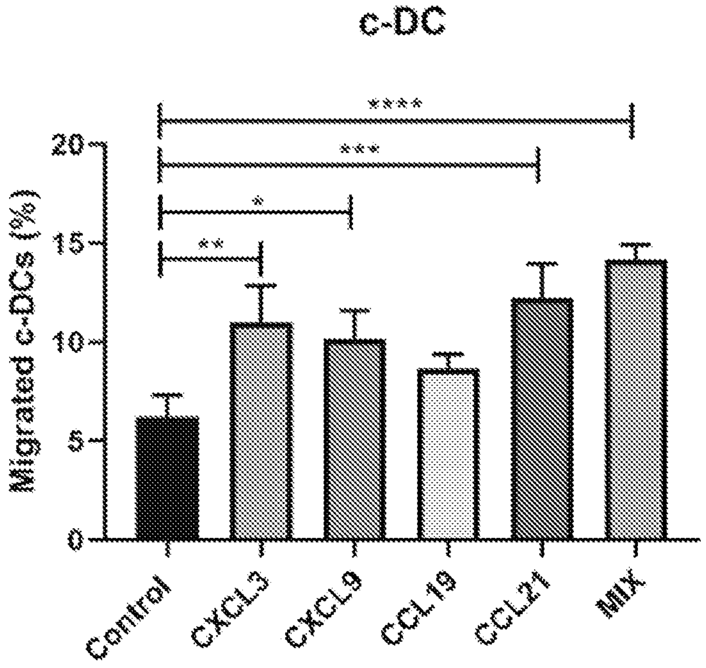

To evaluate chemokine efficacy at activating a DCs various chemokines were tested for stimulation of migration of three types of DCs in an in vitro trans-well migration assay. As shown in FIGS. 3A-3C chemokines CXCL3, CXCL9, CCL19, and CCL21 were tested for migratory stimulation of three types of DCs: bone marrow-derived (BM-DC, FIG. 3A); spleen DC (p-DC, FIG. 3B); and circulating DCs from peripheral blood (c-DC, FIG. 3C). Each type of DC was cultured in the presence of the different chemokines to evaluate chemotaxis potentiality. CXCL9 demonstrated the ability to recruit all three types of DCs, whereas other chemokines could only significantly stimulate one or two types of DCs.

Figure 8A:
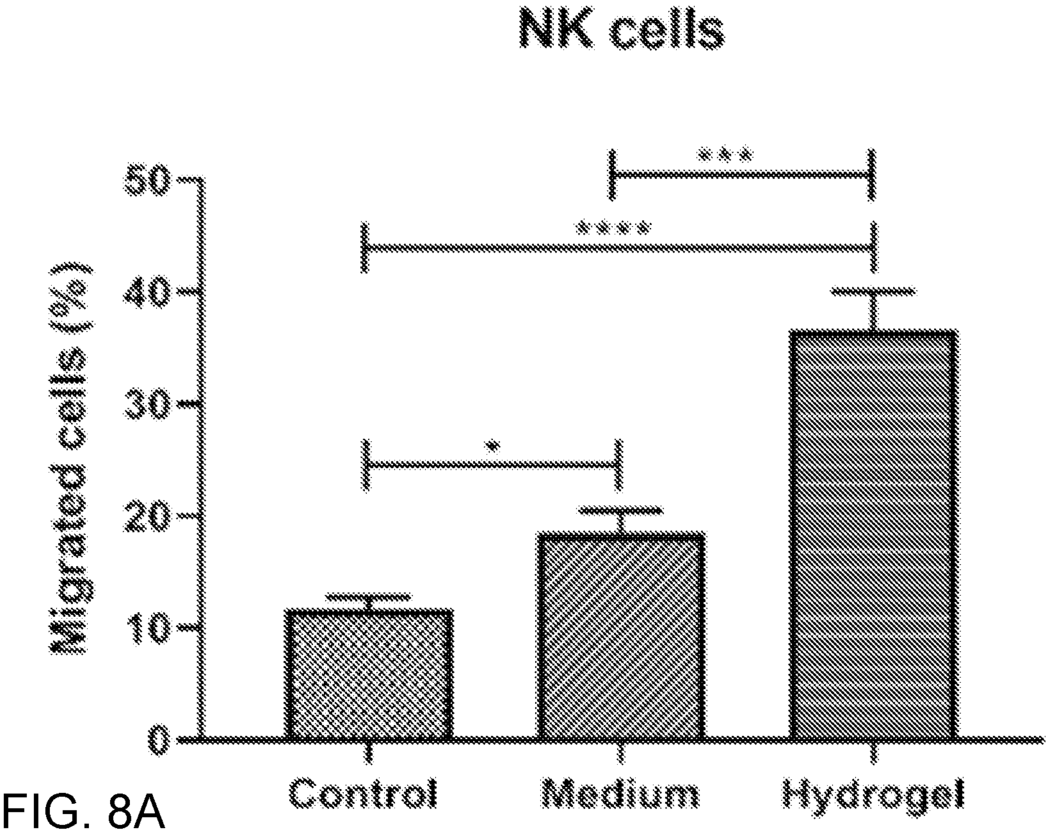
FIGS. 8A-8D illustrate in vitro trans-well migration analysis of natural killer (NK) cells.
Figure 8B:
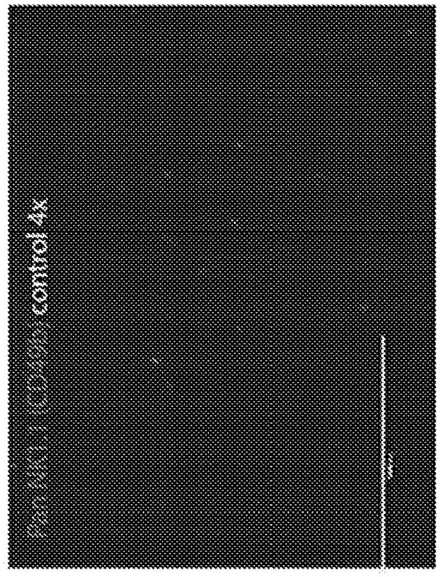
Figure 8C:
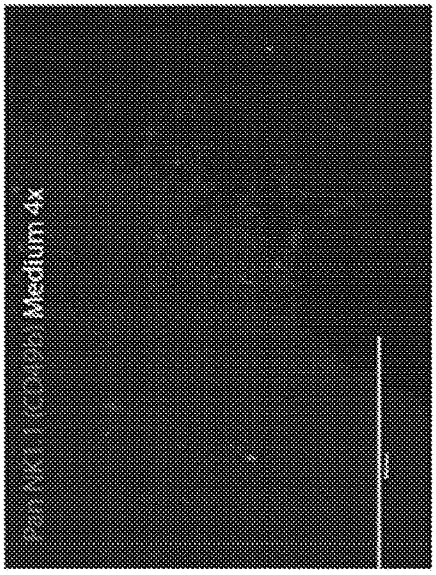
Figure 8D:
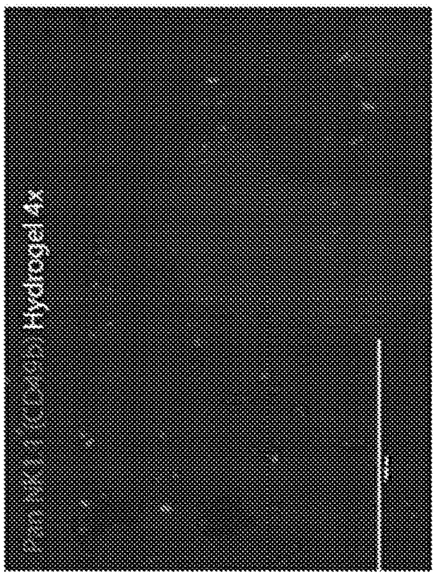
Figure 9A:
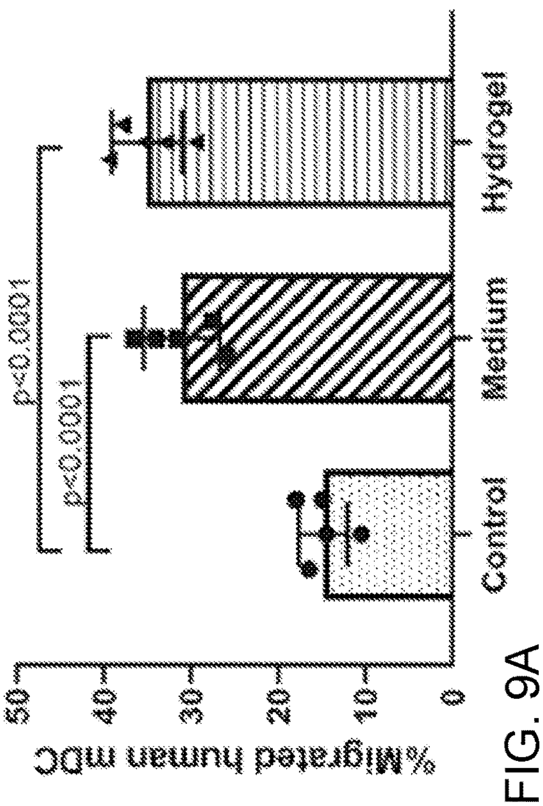
FIGS. 9A-9D illustrate in vitro trans-well migration analysis of human monocyte-derived dendritic cells (h-mDCc).
Figure 9B:
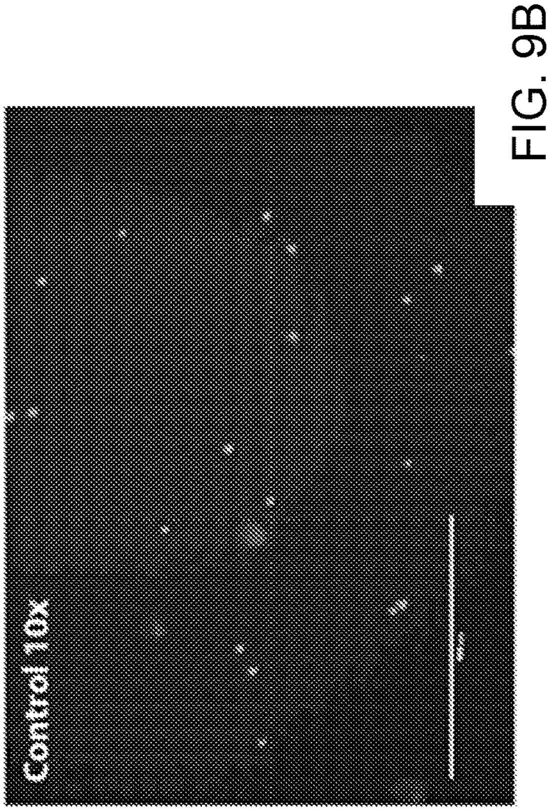
Figure 9C:
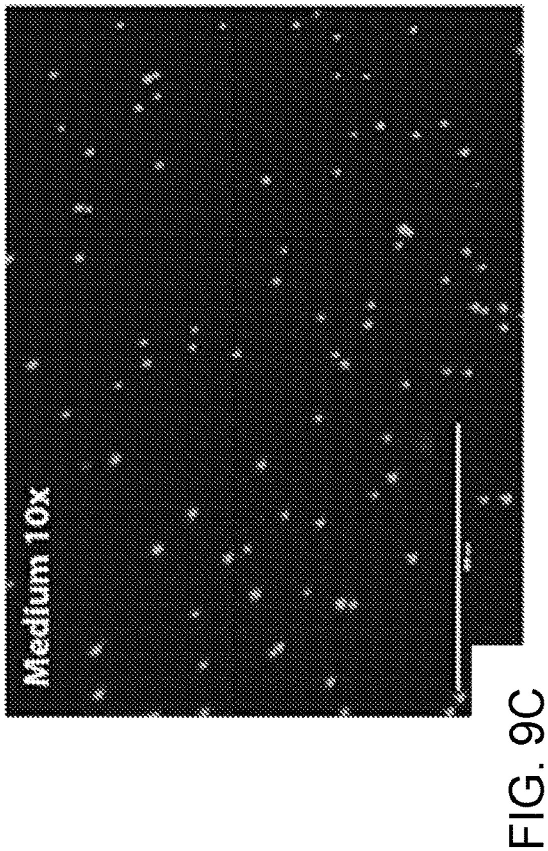
Figure 9D:
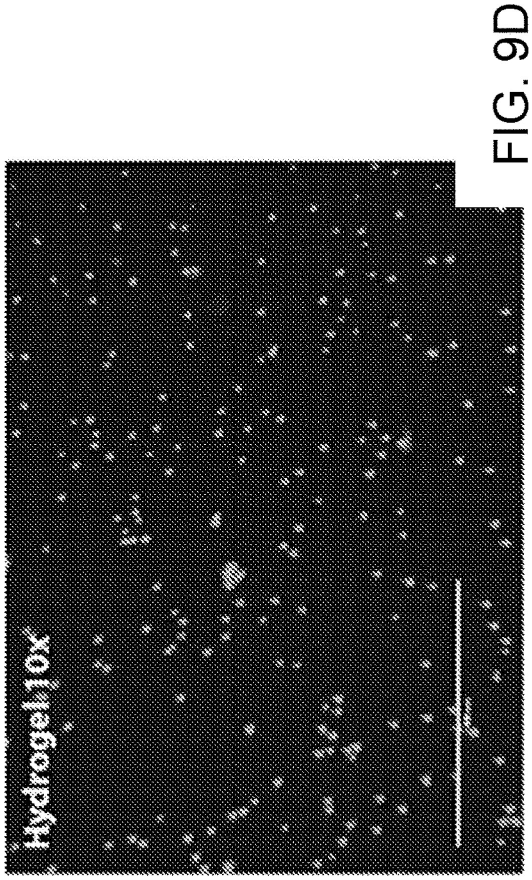
Figure 10A:
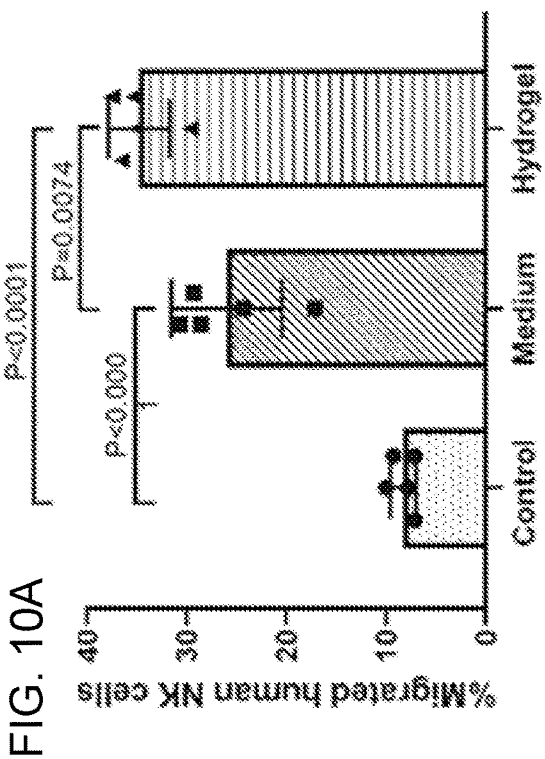
FIGS. 10A-10D illustrate in vitro trans-well migration analysis of human natural killer (h-NK) cells.
Figure 10B:
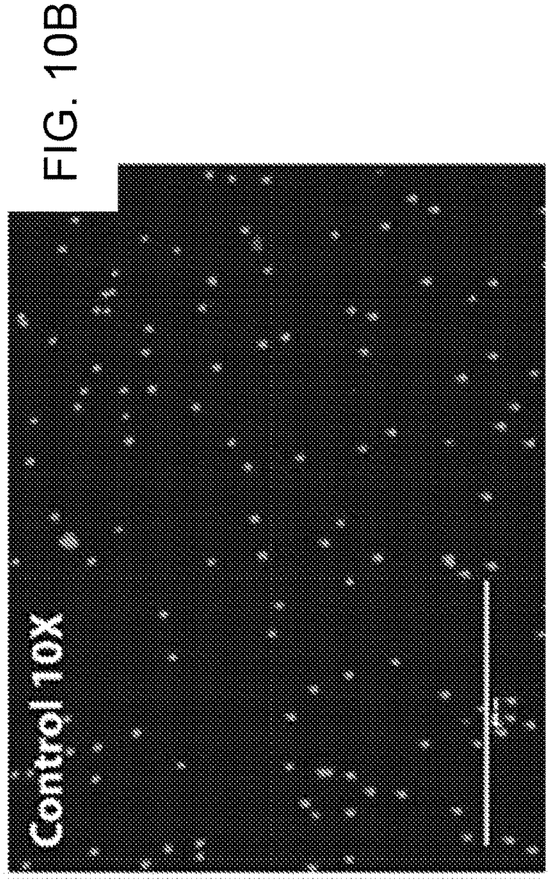
Figure 10C:
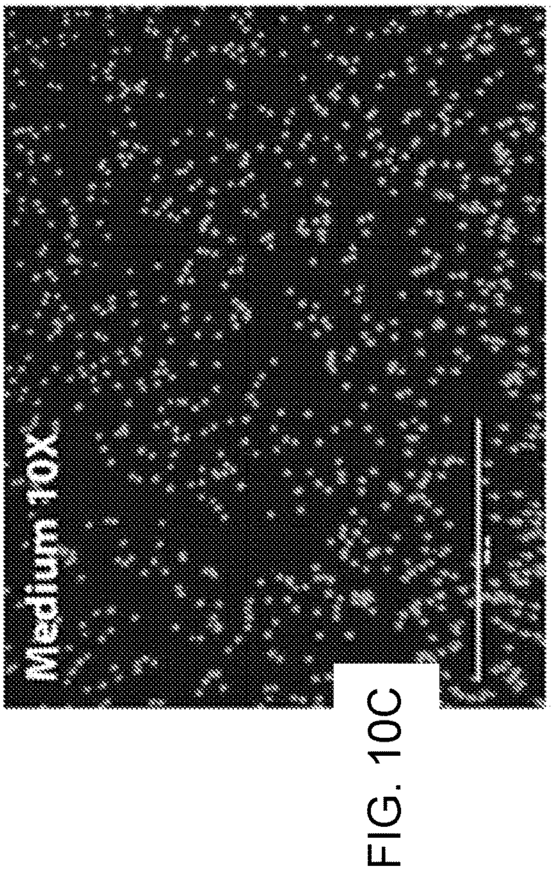
Figure 10D:
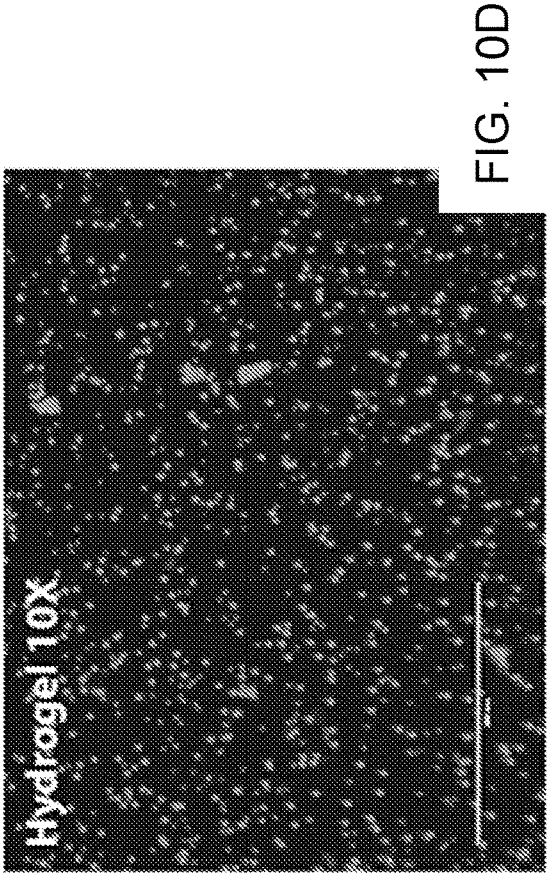

CXCL9 was also shown to recruit natural killer (NK) cells. As shown in FIG. 8A, NK cells could significantly migrate into the hydrogel in comparison to the control, and NK cells migrated into hydrogel more than the culture medium. FIGS. 8B-D illustrate immunofluorescence microscopy observation of the migrated NK cells in the control group (FIG. 8B), in the CXCL9 culture medium group (FIG. 8C), and in the CXCL9 hydrogel group (FIG. 8D). These results demonstrate that both the presence of CXCL9 and the hydrogel provide a superior environment for stimulation and migration of the NK cells.

Figure 6B:
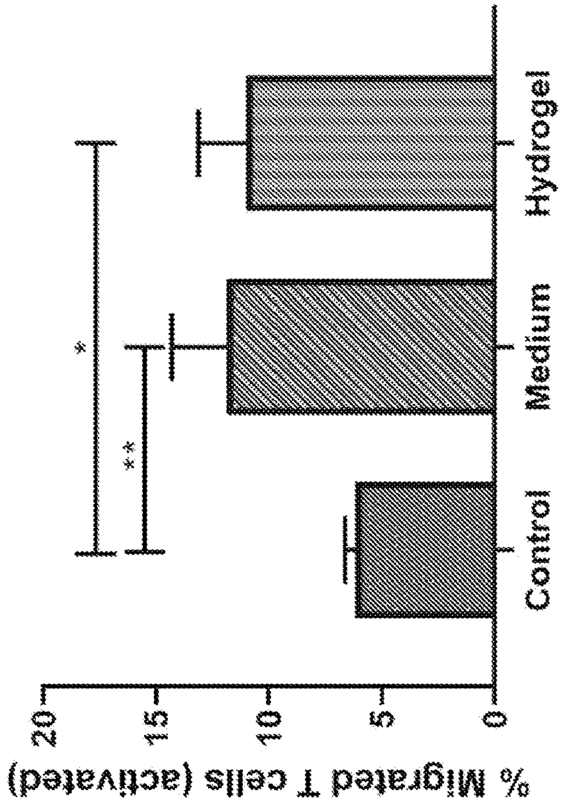
FIGS. 6A-6B are graphs illustrating in vitro trans-well migration analysis of naïve (FIG. 6A) vs. activated (FIG. 6B) T cells.
Figure 6A:
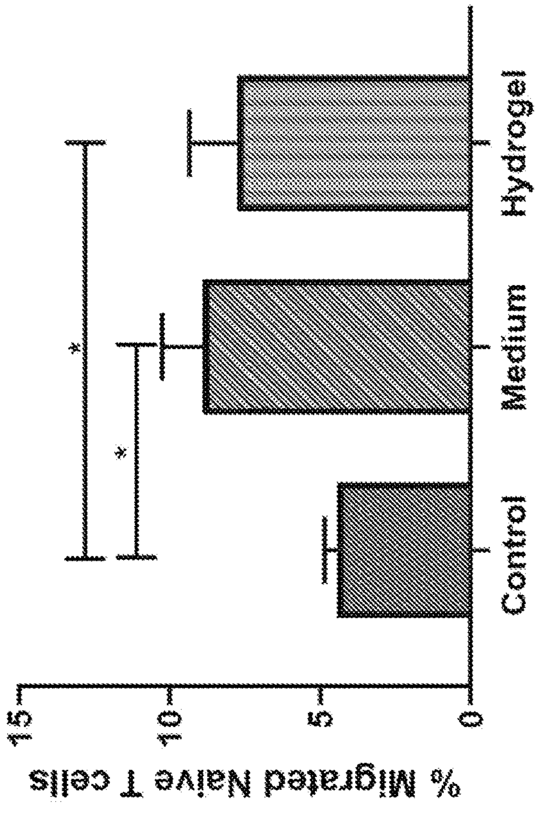

CXCL9 was additionally shown to recruit both naïve and activated T cells in both culture medium and hydrogel, as illustrated in FIGS. 6A-6B. FIGS. 9A-9D also show that h-mDCs could significantly migrate into the hydrogel and culture medium containing CXCL9 in comparison to the control. Human NK cells were also tested in a migration analysis assay, and it was found that these cells significantly migrated into the hydrogel and culture medium containing CXCL9 in comparison to the control. NK cells were also observed, with statistically significant difference, to migrate into hydrogel more than the culture medium (FIGS. 10A-10D).

Figure 7:
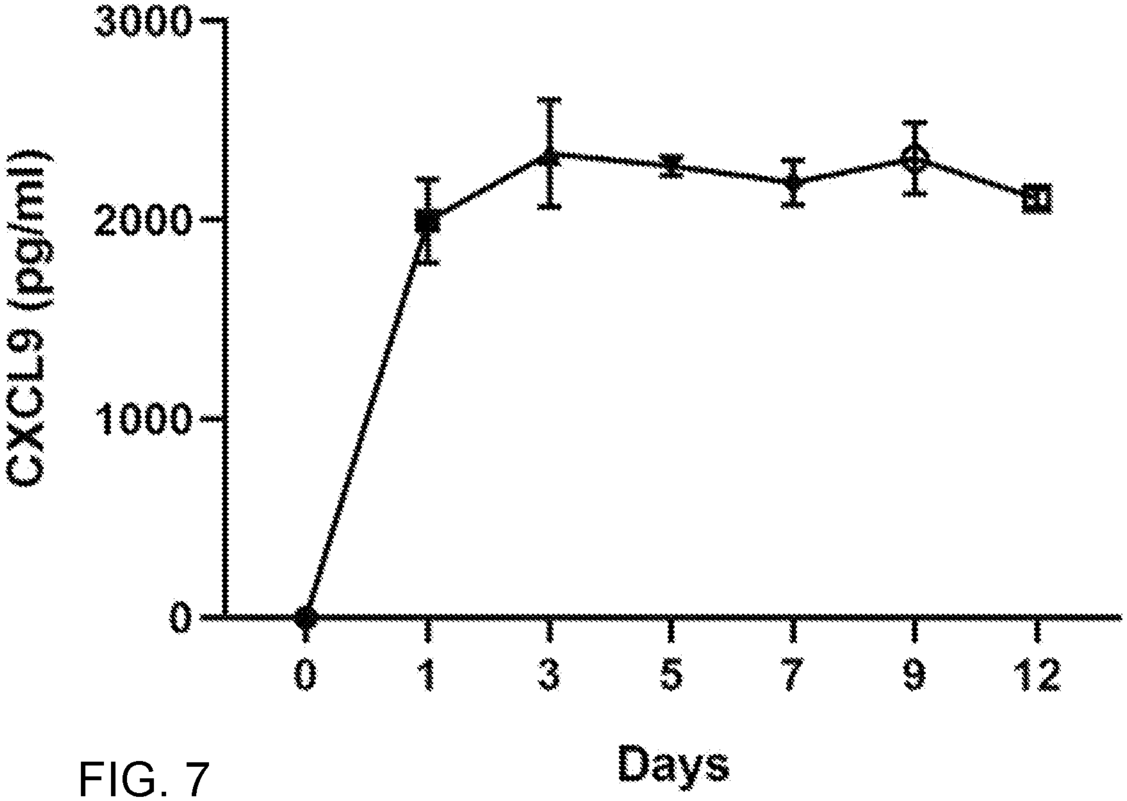
FIG. 7 is a graph illustrating a CXCL9 chemokine releasing assay to evaluate the amount of CXCL9 released from a hydrogel of the present disclosure over time.

The release of CXCL9 from the hydrogel was analyzed and quantified in a release assay described above. The results showed that the designed hydrogel sharply releases the CXCL9 in the first 24 hours and then releasing plateaus and remains steady for at least 12 days, possibly longer (FIG. 7).

Figure 4A:
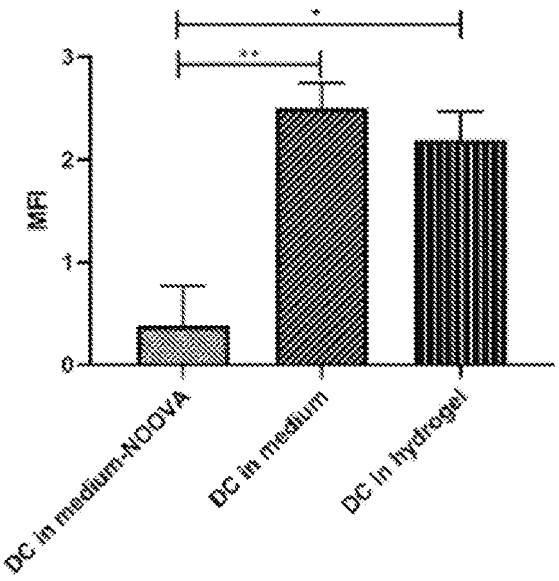
FIGS. 4A and 4B are graphs illustrating measurement of antigen uptake in murine BM-DC in hydrogel vs culture medium.
Figure 4B:
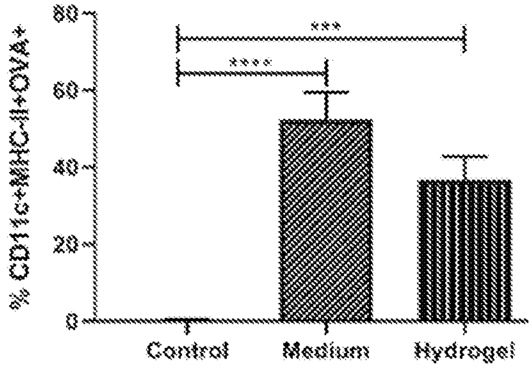
Figure 4C:
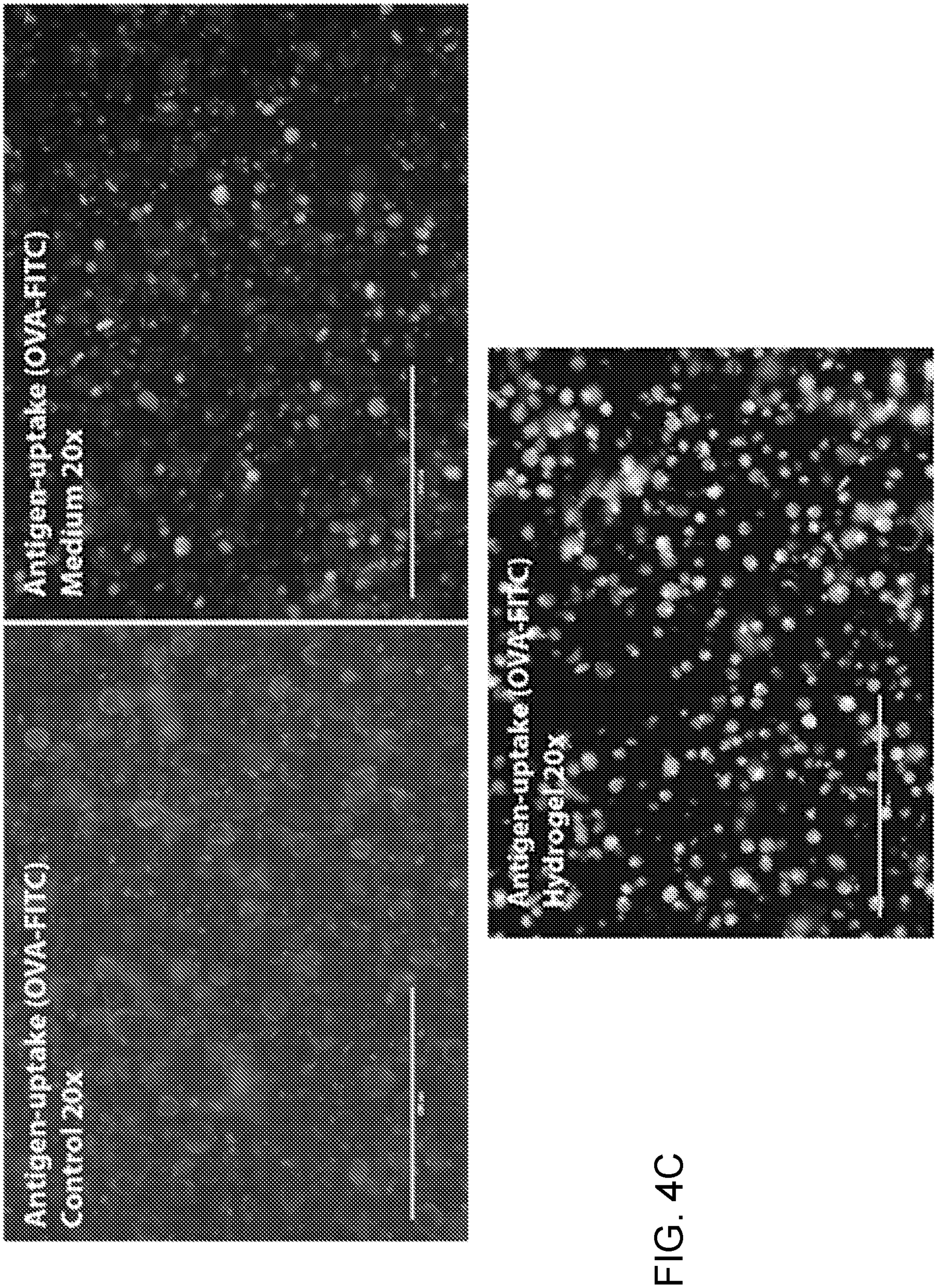
FIG. 4C illustrates images of immunofluorescence microscopy of DCs that uptake OVA-FITC as an antigen.

Antigen uptake by DCs was evaluated to determine ability of DCs to uptake antigen in antigen-containing culture medium and antigen-containing hydrogel. FIG. 4A illustrates that cells in both medium and hydrogel could take up antigen. Mean 2.501 MFI for medium and 2.191 MFI for hydrogel vs 0.3849 for control. ($p=0.0144$, unpaired t test, $n=3$). (FIG. 4B). Immunofluorescence microscopy visualization of OVA-FITC is shown in FIG. 4C. There were not any significant differences to uptake the antigen between DCs loaded into the hydrogel compared to DCs cultured in the medium, and it was determined that both appear to effectively uptake the antigen.

Figure 5A:
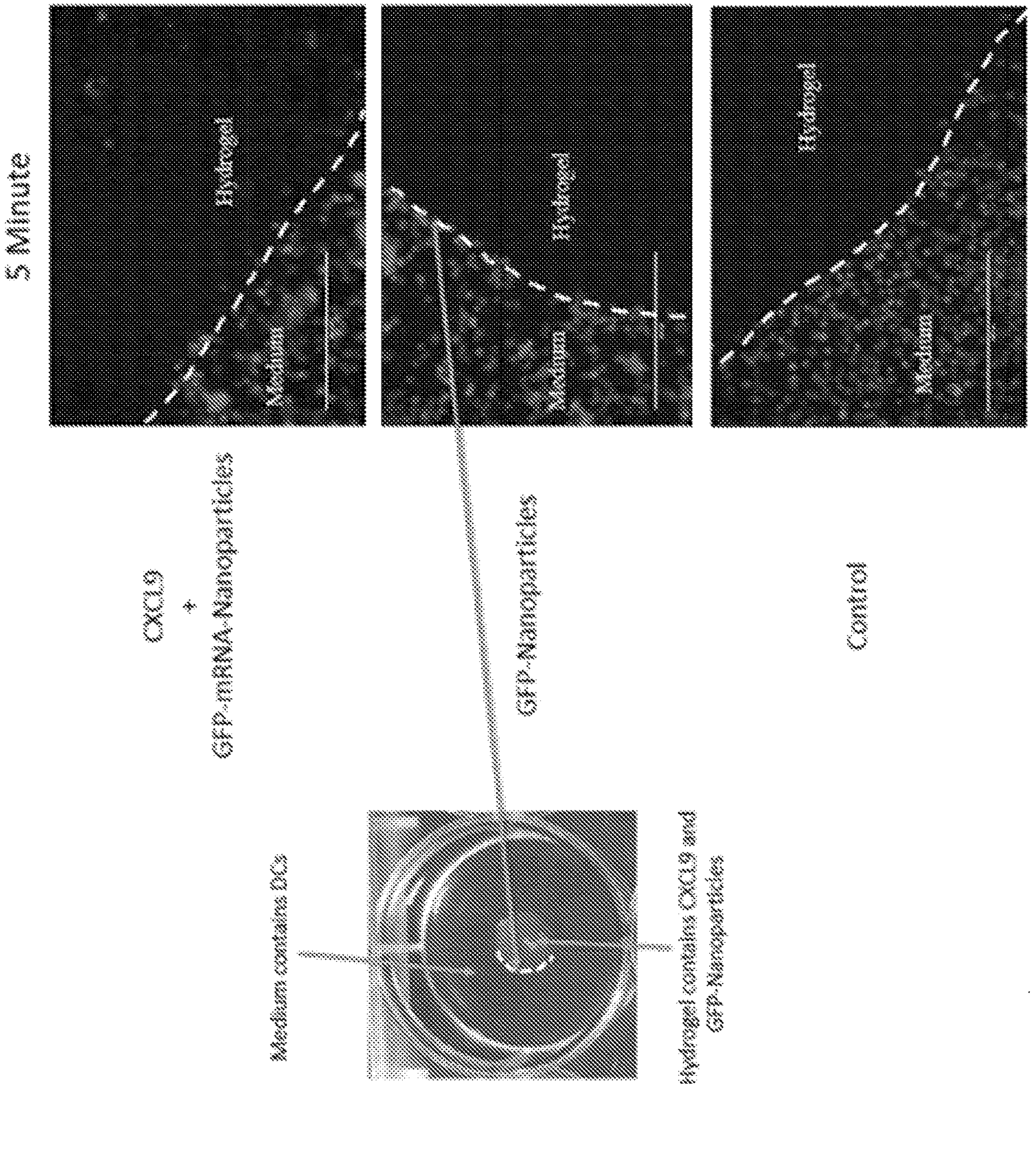
FIGS. 5A-5B illustrate images of an antigen presenting assay performed with DCs migrated into the hydrogel using GFP-mRNA nanoparticles.
Figure 5B:
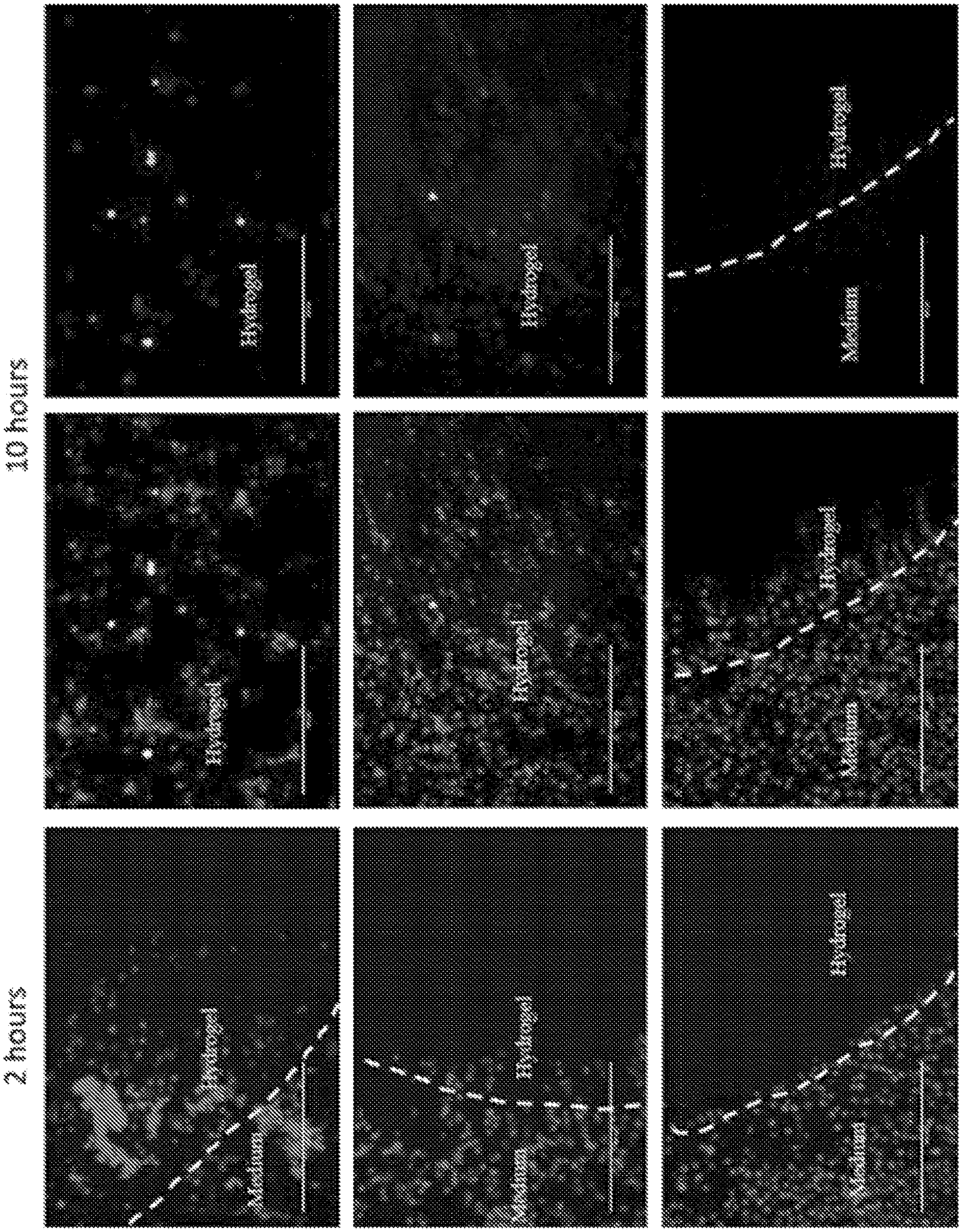

An antigen presenting assay was performed to analyze and visualize DC migration into hydrogel using GFP-mRNA nanoparticles. FIGS. 5A-5B illustrate that DCs migrated into the hydrogel that contains CXCL9 and could uptake the GFP-mRNA-Nanoparticles and express the GFP after 10 hours. The results demonstrate that the target mRNA antigen can be introduce to the migrated DCs inside the hydrogel.

Conclusions

The nanocomposite hydrogel vaccine of the present disclosure can be employed as an in situ modulation alternative to the ex vivo DC vaccine and it represents an innovative immunotherapy strategy with enhanced efficacy and reduced limitations and costs. It is a novel method and composition of materials/agents that can be used for treating human diseases, including cancers and infectious diseases.

Example 2—In Vivo Analysis of Nanocomposite Hydrogel Vaccine

This example describes in vivo testing of embodiments of biocompatible nanocomposite hydrogel vaccines of the present disclosure in animal models. These studies were designed to confirm the ability of the vaccines of the present disclosure to recruit immune cells to the site of hydrogel vaccine implantation, and to analyze immune cell stimulation/activation by the mRNA antigen-containing hydrogel vaccine. Studies also accessed affects vaccine efficacy and on overall survival by the hydrogel vaccine in certain animal tumor models. This example confirms that the approaches described in the present disclosure to modulate a subject's immune cells in situ by designing and using a biocompatible nanocomposite hydrogel vaccine are effective in recruiting host immune cells, stimulating immune response, and improving survival.

Materials and Methods

Hydrogel Preparation

The hydrogel vaccines were prepared in accordance with the methods described in Example 1 above, with the following parameters: 150-375 μg of DOTAP Nano-liposome (with concentration of 2.5 μg/μl) was added on top of 10-25 μg of mRNA (with concentration of 1 μg/μl of PBS) and incubated for about 15 minutes in room temperature. This composition of mRNA loaded nano-liposomes was combined with the 25 wt % hydrogel (as described in table.1). Finally, 500 ng of CXCL9 was loaded into total volume of the hydrogel/liposome composition. Prepared hydrogel vaccine was injected intra mammary fat pad for in vivo migration assay and immune response assessment. Prepared hydrogel vaccine (without mRNA/liposomes) was injected subcutaneous for survival assessment Animal Models For animal experiments, C57BL/6 mice were used. Mice were implanted with various tumors as describe below and some were treated with either hydrogel vaccine or hydrogel control as described below.

Immune Cell Recruitment Assay

C57BL/6 mice underwent implantation of hydrogel vaccine (with or without mRNA antigen) in the mammary fat pad, control group received no treatment. After 3, 5 and 10 days, the fat pad was collected and flow cytometry was used to assess immune cell recruitment. DCs, NK cells and T cells, antigen-specific T cells population, sub-population and absolute numbers were assessed.

Antigen-Specific T Cell Stimulation Assay in Spleen and Tumor

C57BL/6 mice underwent implantation of B16F10-OVA tumor and subcutaneous injection of hydrogel alone (hydrogel control) or hydrogel vaccine with OVA-mRNA antigen. Control animals received no hydrogel treatment. The spleen and tumor were collected, and flow cytometry was used to assess immune response. DCs, NK cells and T cells, antigen-specific T cells population, sub-population and absolute numbers were assessed.

Assessment of Survival in Glioma and Melanoma Brain Tumor Models

C57BL/6 mice received intracranial implants with KR158-luciferase glioma tumor. Hydrogel vaccine was prepared as described above and contained total tumor RNA (ttRNA) antigen. Test groups received either a single dose hydrogel vaccine or a multi-dose of hydrogel vaccine every 5 days for 3 doses, hydrogel control received vaccine without antigen, and control group did not receive vaccine. Survival was assessed, and tumor growth was assessed with IVIS imaging. C57BL/6 mice underwent implantation of B16F10-OVA melanoma tumors in the flank. Test groups were treated with injection of hydrogel vaccine with OVA-mRNA antigen into the mammary fat pad after infusion of OT-1 T cells 2 days after tumor implantation. Survival was assessed, and tumor measurements were performed until the endpoints to assess the tumor growth control.

Analysis of CD4 and CD8 T Cells and NK Cells on Vaccine Efficacy

C57BL/6 mice were implanted intracranially with KR158-luciferase. Animals received either a single dose hydrogel vaccine with total tumor RNA (ttRNA) antigen or the vaccine in combination with one or more CD4/CD8/NK depleting antibodies, CXCL9 alone loaded into hydrogel, or no treatment (control). Survival was assessed in all groups and compared with the control animals.

Results and Discussion

A hydrogel was generated from Polyethylene Glycol (PEG) as described above and tested for in vivo recruitment of immune cells to the site of implantation. The hydrogel vaccine was placed in the mammary fat pad of C57BL/6 mice, which was then later collected and assessed via flow cytometry for recruitment of classic DCs (cDC2), NK cells, plasmacytoid dendritic cells (pDCs), and inflammatory DCs. cDC2 and NK cells were both significantly increased 3 days after vaccination (FIGS. 11A-11B), and pDCs and inflammatory DCs were increased at 5 days post vaccination (FIGS. 11C-11D). The increase in all 4 types of immune cells at the site of vaccination indicates the ability of the hydrogel vaccine to recruit various immune cells to the hydrogel for activation.

Figure 12A:
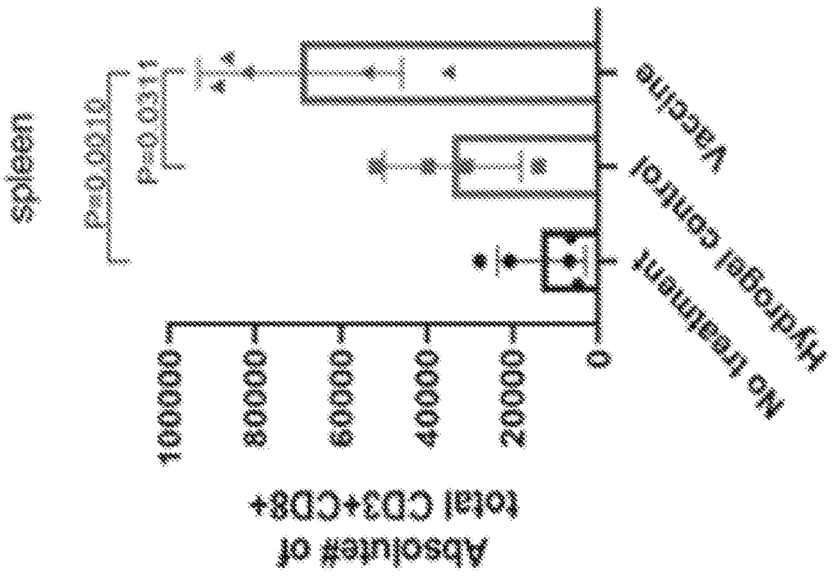
FIGS. 12A-12C are bar graphs illustrating in vivo analysis of antigen-specific T cells stimulation in spleen and tumor microenvironment (TME). The results illustrate that total CD8 T cells increased in spleen (FIG. 12A), and OT-I positive CD8 T cells increased in both spleen (FIG. 12B) and tumor (FIG. 12C).
Figure 12B:
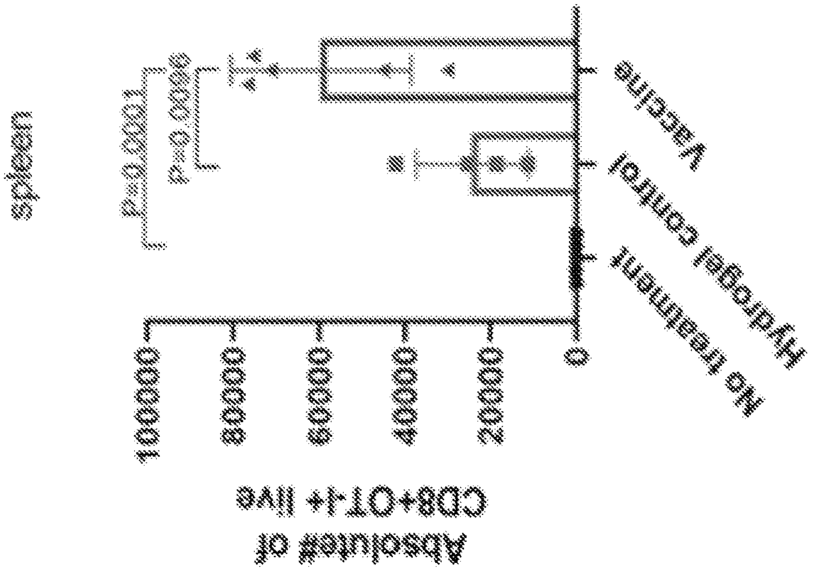
Figure 12C:
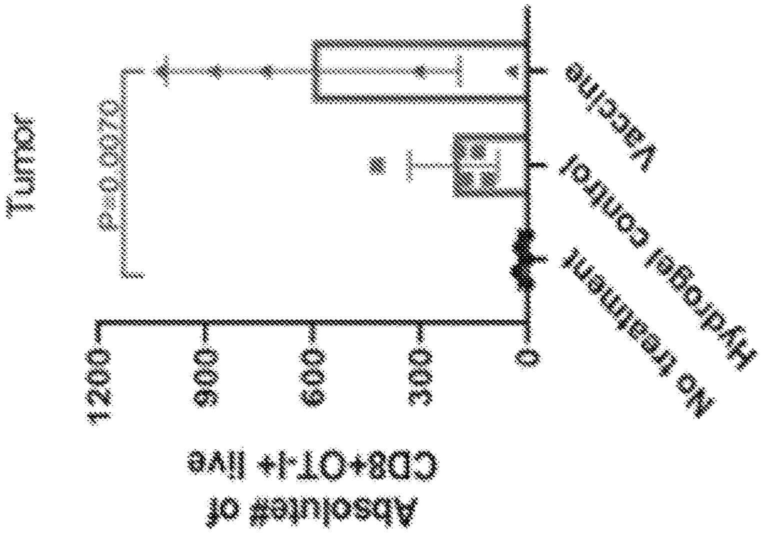

To assess in vivo stimulation of antigen-specific T cells, C57BL/6 mice underwent implantation of B16F10-OVA tumor and subcutaneous injection of hydrogel vaccine with nano liposomes loaded with mRNA corresponding to OVA-antigen. Spleen and Tumor were removed after 3, 5 and 10 days and assessed. Total CD8 T cells increased in spleen (FIG. 12A) and OT-I positive CD8 T cells increased in both spleen (FIG. 12B) and tumor (FIG. 12C). These results demonstrate that the hydrogel vaccine was able to recruit immune cells to the vaccine site to encounter the tumor specific mRNA antigen, which then resulted in production of antigen-specific T cells in the spleen and targeting of those T cells to the tumor site.

Figure 13A:
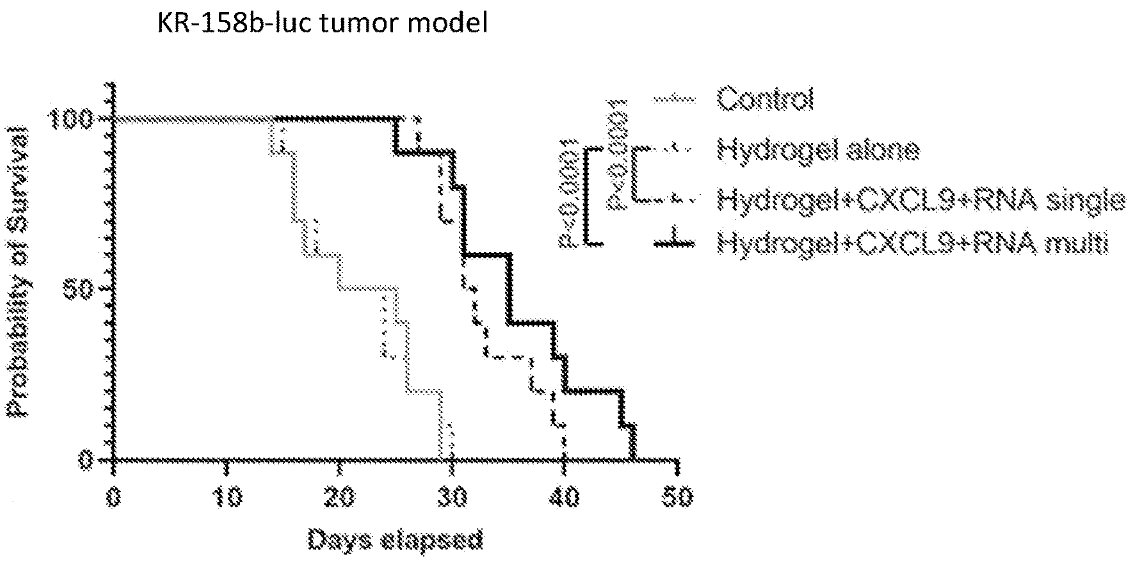
FIGS. 13A-13D illustrate that the hydrogel vaccine improves overall survival in glioma and melanoma brain tumor models. The graph in FIG. 13A illustrates the survival of vaccinated mice vs. control group for a KR-158b-luc tumor model.
Figure 13B:
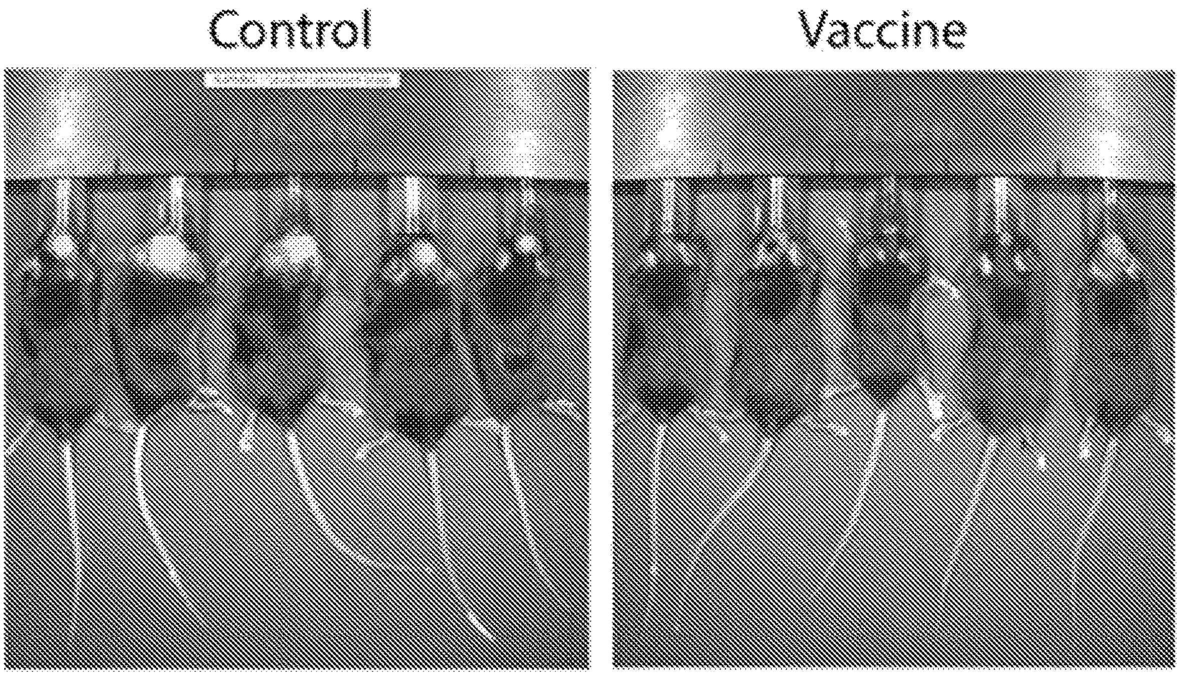
Figure 13C:
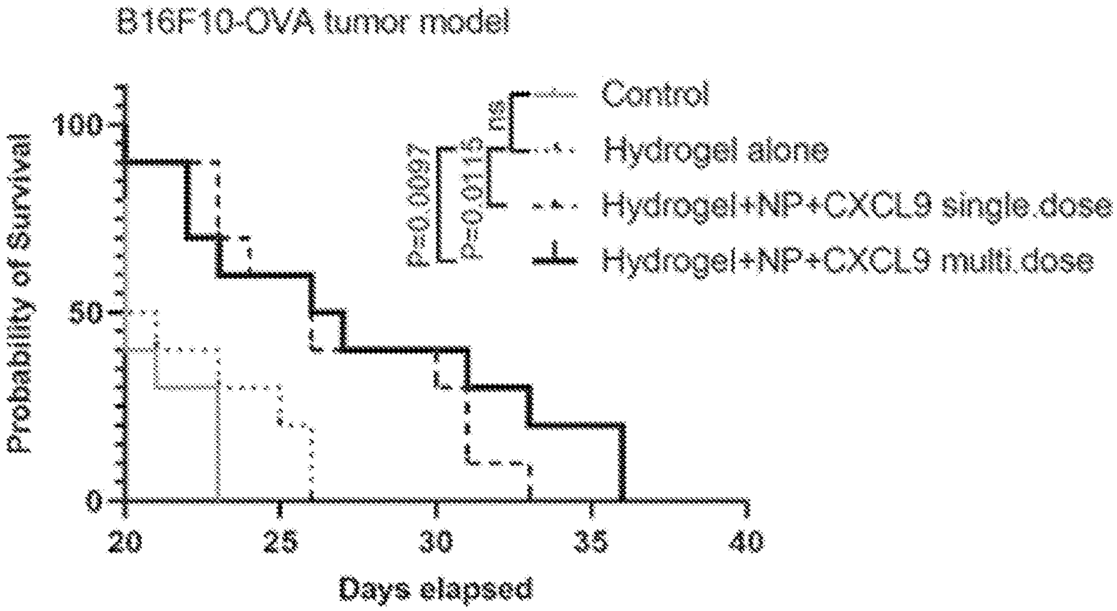
Figure 13D:
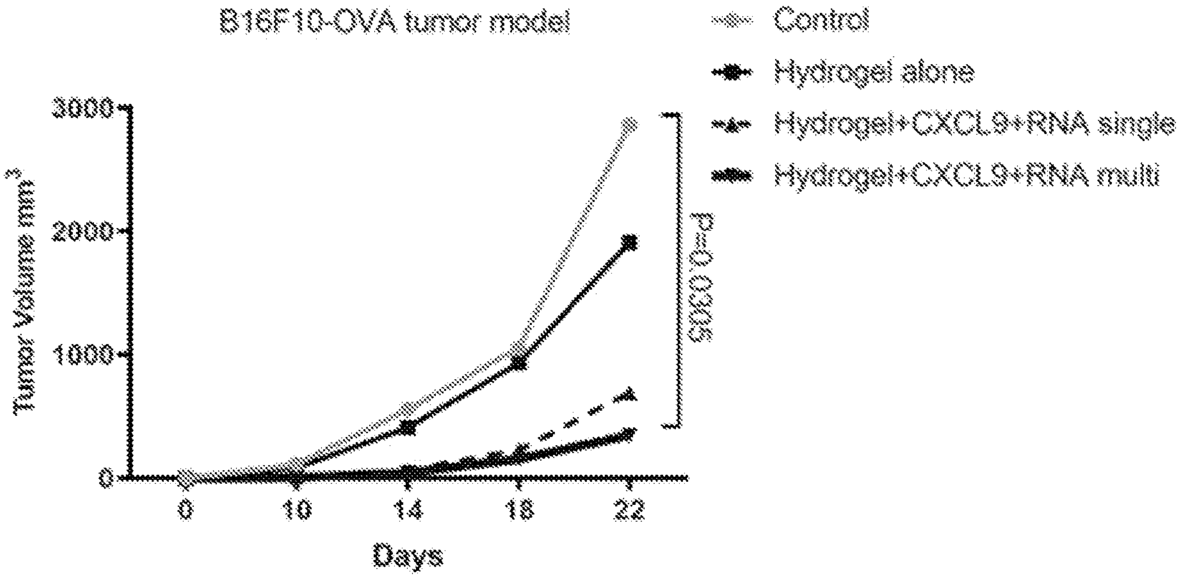

In glioma brain tumor models, KR158-luc implanted mice that received a single dose vaccine containing total tumor RNA or vaccine every 5 days for 3 doses had prolonged survival compared to the control groups (FIG. 13A). IVIS imaging illustrated in FIG. 13B demonstrated that vaccinated animals had reduced tumor growth compared to the control group. FIGS. 13C and 13D show that, for mice that underwent implantation of B16F10-OVA melanoma tumors in the flank, animals that received a vaccine every 5 days for 3 doses had a slight improvement in tumor control and survival compared to the single dose group, and both vaccine groups had greater survivability and reduced tumor grown compared to control groups.

Figure 14:
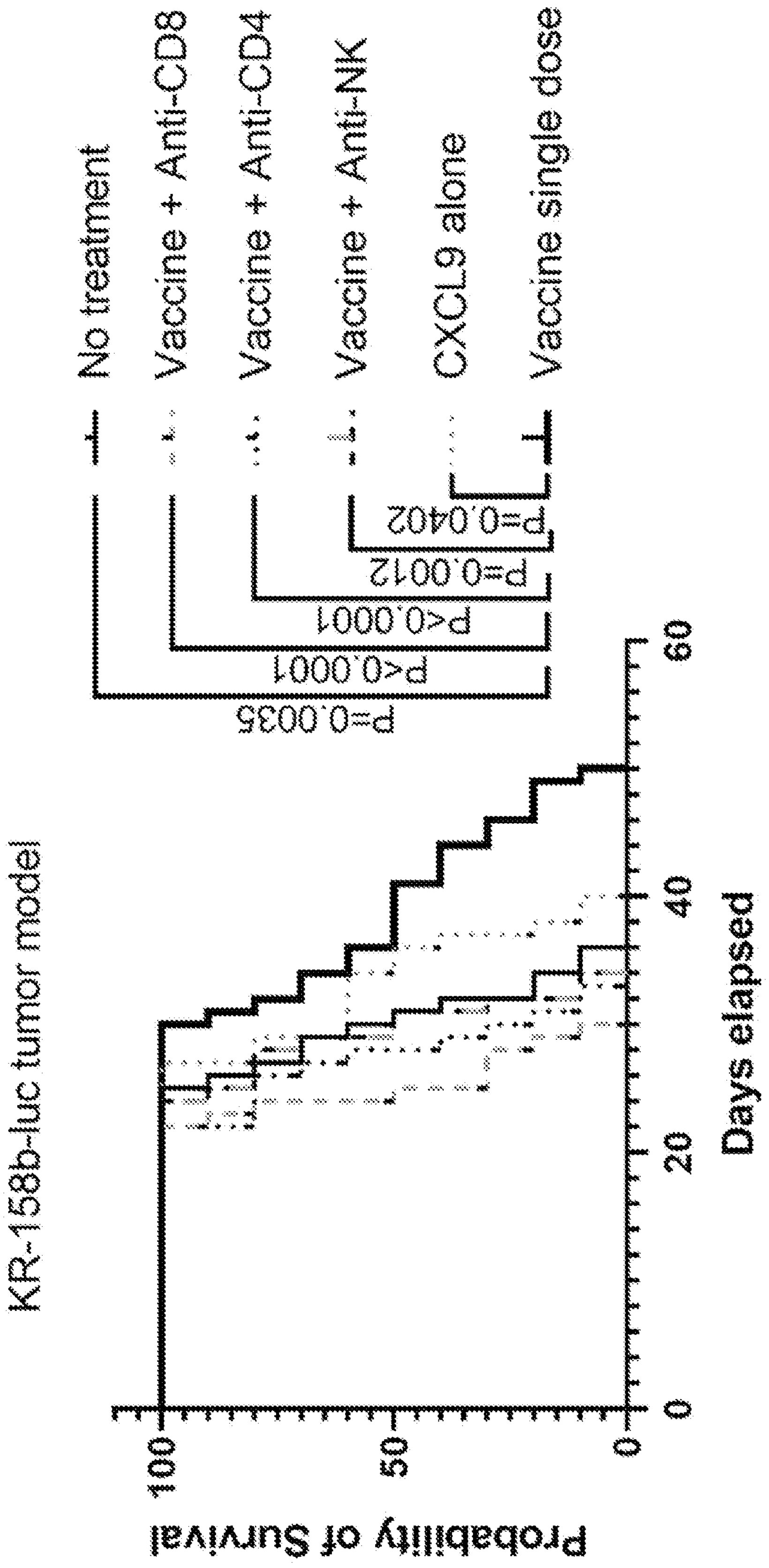
FIG. 14 illustrates that CD4, CD8 T cells and NK cells play a role in hydrogel vaccine efficacy, with reduced vaccine efficacy in CDR/CD8/NK depleted animal models.

Assessment of the role of CD4, CD8, and NK cells on vaccine efficacy is illustrated in FIG. 14. Results show that mice receiving a single does hydrogel vaccine had the greatest survivability, followed by mice dosed with CXCL9 hydrogel alone. However, the hydrogel vaccine did not prolong survival when administered to mice with depletion of CD4, CD8, and/or NK cells, indicating interaction between vaccine and immune cells in the vaccine activity.

REFERENCES

1. Leitner, W. W., Ying, H., & Restifo, N. P. (1999). DNA and RNA-based vaccines: principles, progress and prospects. *Vaccine,* 18(9-10), 765-777. doi:10.1016/s0264-410x(99)00271-6
2. Liu, M. A. (2019). A Comparison of Plasmid DNA and mRNA as Vaccine Technologies. *Vaccines* (*Basel*), 7(2). doi:10.3390/vaccines7020037
3. McNamara, M. A., Nair, S. K., & Holl, E. K. (2015). RNA-Based Vaccines in Cancer Immunotherapy. *J Immunol Res,* 2015, 794528. doi:10.1155/2015/794528
4. Hubert P, Evrard B, Maillard C, et al. Delivery of granulocyte-macrophage colony-stimulating factor in bioadhesive hydrogel stimulates migration of dendritic cells in models of human papillomavirus-associated (pre)neoplastic epithelial lesions. Antimicrob Agents Chemother. 2004; 48(11):4342-4348. doi:10.1128/AAC.48.11.4342-4348.2004
5. Song H, Yang P, Huang P, Zhang C, Kong D, Wang W. Injectable polypeptide hydrogel-based co-delivery of vaccine and immune checkpoint inhibitors improves tumor immunotherapy. *Theranostics.* 2019; 9(8):2299-2314. Published 2019 Apr. 12. doi:10.7150/thno.30577

We claim at least the following:

1. A biocompatible, nanocomposite hydrogel composition consisting of:

phosphate buffered saline (PBS);

a biocompatible hydrogel material, wherein the biocompatible hydrogel material consists of polyethylene glycol (PEG) polymerized with poly(ethylene glycol) diacrylate (PEGDA);

a plurality of CXCL9 molecules; and a plurality of nano liposomes loaded with mRNA molecules corresponding to an antigen for a specific disease, wherein the plurality of mRNA-loaded nano liposomes are in the hydrogel, and wherein the nano liposomes consist of multi-layer vesicles whose lipid portion consists of dioleyl-3-trimethylammonium propane (DOTAP) having a hollow core encapsulating an mRNA composition consisting of the mRNA molecules in PBS.

2. The biocompatible, nanocomposite hydrogel composition of claim 1, wherein the hydrogel material is a microporous hydrogel material.

3. The biocompatible, nanocomposite hydrogel composition of claim 1, wherein the CXCL9 molecules are present in a concentration of about 250 to 1500 ng/ml of the biocompatible, nanocomposite hydrogel composition.

4. The biocompatible, nanocomposite hydrogel composition of claim 1, wherein the mRNA molecules correspond to a tumor antigen.

5. The biocompatible, nanocomposite hydrogel composition of claim 1, wherein the mRNA molecules correspond to an infectious disease antigen.

6. The biocompatible, nanocomposite hydrogel composition of claim 1, wherein the nano liposomes have an average diameter of about 70 nm to 200 nm.

7. The biocompatible, nanocomposite hydrogel composition of claim 1, wherein the mRNA loaded nano liposomes include about 1 μg mRNA loaded in about 5-10 μg of nano liposomes.

8. The biocompatible, nanocomposite hydrogel composition of claim 1, wherein the composition comprises about 5 μg-550 μg mRNA loaded nano liposomes per total volume of biocompatible, nanocomposite hydrogel composition.

9. The biocompatible, nanocomposite hydrogel composition of claim 1 made by the process comprising:

preparing the plurality of mRNA loaded nano liposomes by combining the mRNA molecules corresponding to the antigen in phosphate buffered saline (PBS) with a composition of nano liposomes; and combining the plurality of mRNA loaded nano liposomes with a CXCL9 composition comprising the plurality of CXCL9 molecules and a biocompatible hydrogel material to form the biocompatible, nanocomposite hydrogel composition.

10. The biocompatible, nanocomposite hydrogel composition of claim 9, wherein the mRNA molecules and composition of nano liposomes are combined in a ratio of about 1:6 (mRNA molecules: nano liposomes).

11. The biocompatible, nanocomposite hydrogel composition of claim 9, wherein the CXCL9 composition is added to the mRNA loaded nano liposomes to form a mRNA-nano liposome-CXCL9 composition prior to combining with the biocompatible hydrogel material, and wherein the mRNA-nano-liposome-CXCL9 composition and the biocompatible hydrogel material are combined in a ratio of about 1:1 (v/v).

12. The biocompatible, nanocomposite hydrogel composition of claim 9, wherein the biocompatible, nanocomposite hydrogel composition includes about 50 to 60% by volume biocompatible hydrogel material, about 30 to 40% by volume nano liposomes, about 10 to 20% by volume PBS, about 5 to 10 ppm of mRNA per total volume and about 0.25 to 1.5 ppm of CXCL9 per total biocompatible, nanocomposite hydrogel composition volume.

13. A vaccine comprising the biocompatible nanocomposite hydrogel of claim 1.

14. The vaccine of claim 13, comprising about 10 μg of mRNA per vaccine.

15. A method of treating or preventing a disease in a subject, the method comprising: administering a biocompatible nanocomposite hydrogel vaccine, wherein the vaccine comprises the biocompatible nanocomposite hydrogel of claim 1, wherein the disease is cancer and wherein the mRNA antigen is from a tumor cell associated with the cancer.

16. The method of claim 15, wherein the mRNA antigen is derived from a tumor cell in the subject to be treated.

* * * * *